US008932345B2

(12) United States Patent
Moore et al.

(10) Patent No.: US 8,932,345 B2
(45) Date of Patent: Jan. 13, 2015

(54) MEDICAL DEVICE COATINGS FOR RELEASING A THERAPEUTIC AGENT AT MULTIPLE RATES

(75) Inventors: William F. Moore, Bloomington, IN (US); Gary Bradford Shirley, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 12/025,495

(22) Filed: Feb. 4, 2008

(65) Prior Publication Data

US 2008/0195079 A1 Aug. 14, 2008

Related U.S. Application Data

(60) Provisional application No. 60/888,645, filed on Feb. 7, 2007.

(51) Int. Cl.
| | |
|---|---|
| *A61F 2/06* | (2013.01) |
| *A61L 33/00* | (2006.01) |
| *B05D 3/00* | (2006.01) |
| *A61L 27/34* | (2006.01) |
| *A61L 27/54* | (2006.01) |

(Continued)

(52) U.S. Cl.
CPC .............. *A61L 27/34* (2013.01); *A61L 27/54* (2013.01); *A61L 31/10* (2013.01); *A61L 31/16* (2013.01); *A61L 2300/416* (2013.01)
USPC ....... 623/1.46; 623/1.42; 623/1.43; 427/2.24; 427/2.25; 427/2.3

(58) Field of Classification Search
USPC ............. 623/1.1–1.54, 96.01; 427/2.24–2.25, 427/2.28, 2.3; 604/96.01
See application file for complete search history.

(56) References Cited

U.S. PATENT DOCUMENTS

| 5,380,299 A | 1/1995 | Fearnot et al. ............... 604/265 |
| 5,443,458 A | 8/1995 | Eury .......................... 604/891.1 |

(Continued)

FOREIGN PATENT DOCUMENTS

| WO | WO 02/083039 A | 10/2002 |
| WO | WO 2007/095167 A | 8/2007 |

OTHER PUBLICATIONS

International Search Report for PCT/US2008/001455.

*Primary Examiner* — David Isabella
*Assistant Examiner* — Jacqueline Woznicki
(74) *Attorney, Agent, or Firm* — Brinks Gilson & Lione

(57) ABSTRACT

Medical device coatings are provided that simultaneously release a therapeutic agent at different rates from different portions of the medical device coating. In a first embodiment, medical device coatings are provided that include particles comprising a therapeutic agent with two or more different particles sizes within a single layer on a surface of the implantable device. In a second embodiment, medical device coatings are provided having a higher concentration of the therapeutic agent in a first region of the coating than in a second region of the coating. In a third embodiment, medical device coatings are provided that are formed by certain coating processes wherein the droplet size of a spray coating solution is changed during the coating process. These coating processes preferably include applying a solution comprising a therapeutic agent and a suitable solvent to a surface of an implantable medical device. In a fourth embodiment, methods of treatment are provided that include implanting a coated medical device.

21 Claims, 7 Drawing Sheets

(51) Int. Cl.
*A61L 31/10* (2006.01)
*A61L 31/16* (2006.01)
*A41D 19/00* (2006.01)

(56) References Cited

U.S. PATENT DOCUMENTS

| | | | |
|---|---|---|---|
| 5,447,724 A | 9/1995 | Helmus et al. | 424/426 |
| 5,464,650 A | 11/1995 | Berg et al. | 427/2.3 |
| 5,512,055 A | 4/1996 | Domb et al. | 604/265 |
| 5,545,208 A | 8/1996 | Wolff et al. | 623/1 |
| 5,609,629 A | 3/1997 | Fearnot et al. | 623/1 |
| 5,667,764 A | 9/1997 | Kopia et al. | 424/1.45 |
| 5,824,049 A * | 10/1998 | Ragheb et al. | 623/1.44 |
| 5,824,949 A | 10/1998 | Schach | 174/52.1 |
| 5,837,313 A * | 11/1998 | Ding et al. | 427/2.21 |
| 5,865,814 A | 2/1999 | Tuch | 604/265 |
| 5,873,313 A | 2/1999 | Minami et al. | 110/220 |
| 5,873,904 A | 2/1999 | Ragheb et al. | 623/1 |
| 6,096,070 A | 8/2000 | Ragheb et al. | 623/1 |
| 6,120,536 A | 9/2000 | Ding et al. | 623/1.43 |
| 6,258,121 B1 | 7/2001 | Yang et al. | 623/1.46 |
| 6,280,411 B1 * | 8/2001 | Lennox | 604/103.05 |
| 6,299,604 B1 | 10/2001 | Ragheb et al. | 604/265 |
| 6,530,951 B1 | 3/2003 | Bates et al. | 623/1.45 |
| 6,589,546 B2 | 7/2003 | Kamath et al. | 424/423 |
| 6,599,275 B1 | 7/2003 | Fischer, Jr. | 604/265 |
| 6,663,662 B2 | 12/2003 | Pacetti et al. | 623/1.13 |
| 6,730,064 B2 | 5/2004 | Ragheb et al. | 604/265 |
| 6,749,626 B1 * | 6/2004 | Bhat et al. | 623/1.1 |
| 6,770,729 B2 | 8/2004 | Van Antwerp | 528/77 |
| 6,774,278 B1 | 8/2004 | Ragheb et al. | 623/1 |
| 6,887,265 B2 | 5/2005 | Richter et al. | 623/1.15 |
| 6,887,510 B2 | 5/2005 | Villareal | 427/2.24 |
| 6,890,351 B2 | 5/2005 | Termin et al. | 623/1.38 |
| 6,890,395 B2 | 5/2005 | Simhambhatla | 156/218 |
| 6,918,927 B2 | 7/2005 | Bates et al. | 623/1.15 |
| 7,169,178 B1 * | 1/2007 | Santos et al. | 623/1.42 |
| 2002/0013298 A1 * | 1/2002 | Hunter | 514/113 |
| 2002/0082680 A1 | 6/2002 | Shanley et al. | 623/1.16 |
| 2003/0028243 A1 | 2/2003 | Bates et al. | 623/1.15 |
| 2003/0028244 A1 | 2/2003 | Bates et al. | 623/1.15 |
| 2003/0033007 A1 | 2/2003 | Sirhan et al. | |
| 2003/0036794 A1 | 2/2003 | Ragheb et al. | 623/1.15 |
| 2003/0194442 A1 * | 10/2003 | Guivarch et al. | 424/489 |
| 2003/0216699 A1 | 11/2003 | Falotico | |
| 2003/0236513 A1 | 12/2003 | Schwarz et al. | 604/890.1 |
| 2004/0039441 A1 | 2/2004 | Rowland et al. | 623/1.42 |
| 2004/0047909 A1 | 3/2004 | Ragheb et al. | 424/471 |
| 2004/0068241 A1 | 4/2004 | Fischer, Jr. | 604/265 |
| 2004/0073284 A1 | 4/2004 | Bates et al. | 623/1.11 |
| 2004/0127977 A1 | 7/2004 | Shanley | |
| 2004/0137066 A1 * | 7/2004 | Jayaraman | 424/486 |
| 2004/0156872 A1 * | 8/2004 | Bosch et al. | 424/400 |
| 2004/0181278 A1 | 9/2004 | Tseng et al. | 623/1.46 |
| 2004/0210208 A1 | 10/2004 | Paul et al. | 604/500 |
| 2004/0210289 A1 * | 10/2004 | Wang et al. | 607/116 |
| 2004/0243225 A1 | 12/2004 | Ragheb et al. | 623/1.42 |
| 2004/0260318 A1 * | 12/2004 | Hunter et al. | 606/153 |
| 2005/0085898 A1 | 4/2005 | Boatman | 623/1.15 |
| 2005/0087520 A1 | 4/2005 | Wang et al. | 219/121.69 |
| 2005/0090856 A1 | 4/2005 | Porter | 606/200 |
| 2005/0090861 A1 | 4/2005 | Porter | 606/213 |
| 2005/0095267 A1 | 5/2005 | Campbell et al. | 424/425 |
| 2005/0096388 A1 | 5/2005 | Hunter et al. | 514/509 |
| 2005/0096730 A1 | 5/2005 | Villareal | 623/1.15 |
| 2005/0096731 A1 | 5/2005 | Looi et al. | 623/1.16 |
| 2005/0098097 A1 | 5/2005 | Chen et al. | 118/302 |
| 2005/0101635 A1 | 5/2005 | Hunter et al. | 514/332 |
| 2005/0106203 A1 | 5/2005 | Roorda et al. | 424/423 |
| 2005/0106210 A1 | 5/2005 | Ding et al. | 424/423 |
| 2005/0107291 A1 | 5/2005 | Hunter et al. | 514/11 |
| 2005/0107870 A1 * | 5/2005 | Wang et al. | 623/1.44 |
| 2005/0112101 A1 | 5/2005 | Hajjar et al. | 424/93.2 |
| 2005/0112172 A1 | 5/2005 | Pacetti | 424/423 |
| 2005/0112195 A1 | 5/2005 | Cruz et al. | 424/464 |
| 2005/0113903 A1 | 5/2005 | Rosenthal et al. | 623/1.15 |
| 2005/0113907 A1 | 5/2005 | Fischell | 623/1.42 |
| 2005/0113909 A1 | 5/2005 | Shannon et al. | 623/1.46 |
| 2005/0113910 A1 | 5/2005 | Paniagua et al. | 623/2.14 |
| 2005/0123582 A1 | 6/2005 | Sung et al. | 424/426 |
| 2005/0123605 A1 | 6/2005 | Hunter et al. | 424/464 |
| 2005/0129729 A1 | 6/2005 | Schreiner | 424/423 |
| 2005/0129731 A1 | 6/2005 | Horres et al. | 424/423 |
| 2005/0129736 A1 | 6/2005 | Hunter et al. | 424/426 |
| 2005/0131201 A1 | 6/2005 | Pacetti et al. | 528/272 |
| 2005/0131528 A1 | 6/2005 | Buscemi et al. | 623/1.15 |
| 2005/0131532 A1 | 6/2005 | Sirhan et al. | 623/1.42 |
| 2005/0158274 A1 | 7/2005 | Hunter et al. | 424/78.38 |
| 2005/0158356 A1 | 7/2005 | Hunter et al. | 424/423 |
| 2005/0158359 A1 | 7/2005 | Epstein et al. | 424/423 |
| 2005/0158361 A1 | 7/2005 | Dhondt et al. | 424/425 |
| 2005/0158363 A1 | 7/2005 | Shalaby | 424/426 |
| 2005/0159809 A1 | 7/2005 | Hezi-Yamit et al. | 623/1.42 |
| 2005/0163821 A1 | 7/2005 | Sung et al. | 424/426 |
| 2005/0165467 A1 | 7/2005 | Hunter et al. | 623/1.13 |
| 2005/0165472 A1 | 7/2005 | Glocker | 623/1.15 |
| 2005/0165488 A1 | 7/2005 | Hunter et al. | 623/17.16 |
| 2005/0166841 A1 | 8/2005 | Robida | 118/500 |
| 2005/0169958 A1 | 8/2005 | Hunter et al. | 424/423 |
| 2005/0169959 A1 | 8/2005 | Hunter et al. | 424/423 |
| 2005/0169961 A1 | 8/2005 | Hunter et al. | 424/423 |
| 2005/0169969 A1 | 8/2005 | Li et al. | 424/426 |
| 2005/0171593 A1 | 8/2005 | Whirley et al. | 623/1.13 |
| 2005/0171594 A1 | 8/2005 | Machan et al. | 623/1.15 |
| 2005/0171595 A1 | 8/2005 | Feldman et al. | 623/1.15 |
| 2005/0171596 A1 | 8/2005 | Furst et al. | 623/1.15 |
| 2005/0222677 A1 | 10/2005 | Bates et al. | 623/1.42 |
| 2005/0278021 A1 | 12/2005 | Bates et al. | 623/1.44 |
| 2006/0025726 A1 | 2/2006 | Fischer, Jr. et al. | 604/265 |
| 2006/0030826 A1 | 2/2006 | Fischer, Jr. et al. | 604/265 |
| 2006/0052757 A1 | 3/2006 | Fischer, Jr. et al. | 604/265 |
| 2006/0100695 A1 * | 5/2006 | Peacock et al. | 623/1.42 |
| 2006/0198940 A1 * | 9/2006 | McMorrow | 427/2.1 |
| 2007/0161967 A1 | 7/2007 | Fischer, Jr. et al. | 604/508 |
| 2007/0161968 A1 | 7/2007 | Fischer, Jr. et al. | 604/508 |
| 2007/0200268 A1 * | 8/2007 | Dave | 264/109 |
| 2008/0190363 A1 * | 8/2008 | Chen et al. | 118/325 |

* cited by examiner

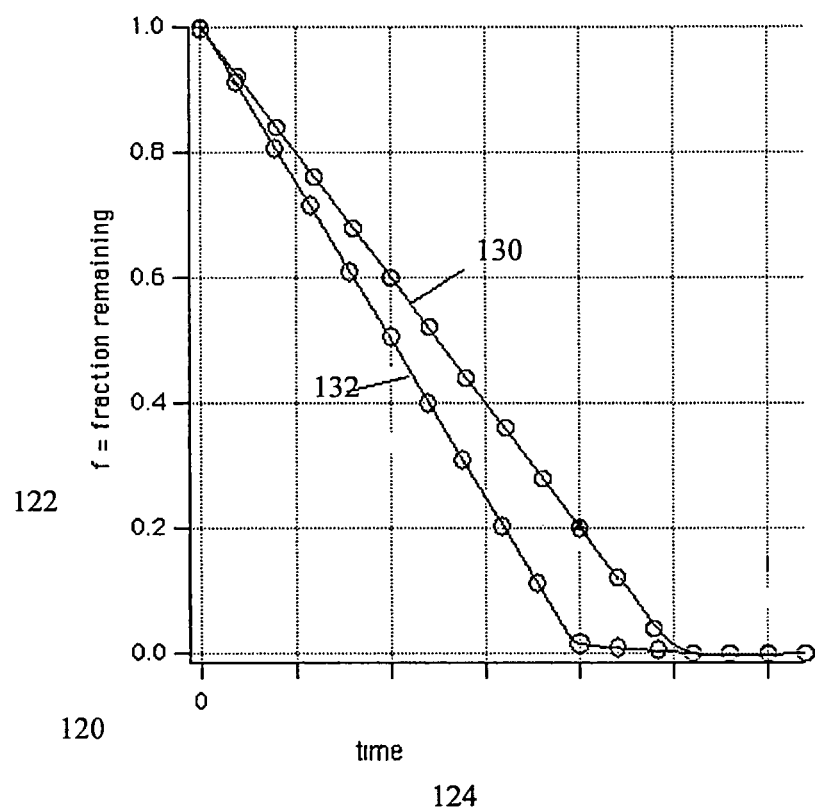

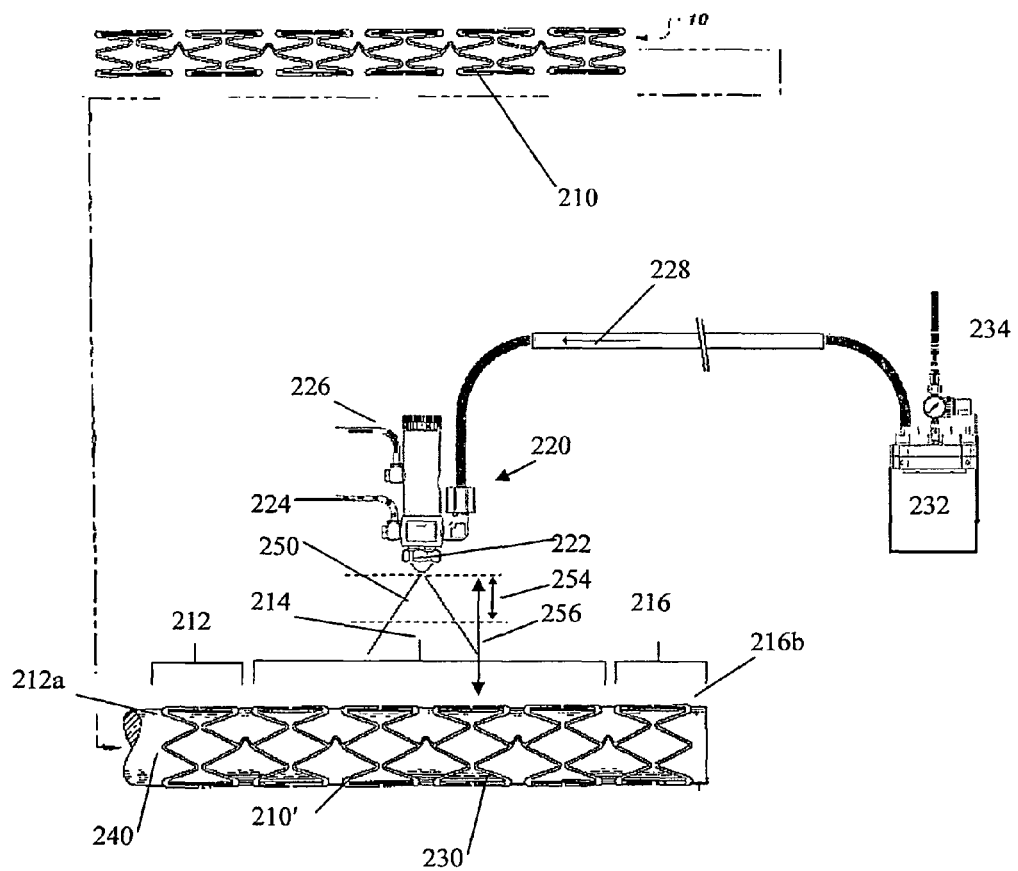

310

320

400

404

408

MEDICAL DEVICE COATINGS FOR RELEASING A THERAPEUTIC AGENT AT MULTIPLE RATES

RELATED APPLICATIONS

This application claims the benefit of U.S. provisional patent application 60/888,645, filed Feb. 7, 2007, which is incorporated herein in its entirety.

TECHNICAL FIELD

The present disclosure relates to therapeutic agent coatings for implantable medical devices, including stents. Preferred medical device coatings are adapted to simultaneously release the therapeutic agent(s) at two or more different rates from different portions of a coating.

BACKGROUND

Delivery of a therapeutic agent from an implantable medical device can be desirable for a variety of applications. Therapeutic agents can be released from a medical device, such as an expandable stent or valve, to treat or mitigate undesirable conditions including restenosis, tumor formation or thrombosis. Procedures for mitigating certain conditions can include implantation of a device comprising a therapeutic agent. For example, the implantation of stents during angioplasty procedures has substantially advanced the treatment of occluded body vessels. Angioplasty procedures such as Percutaneous Transluminal Coronary Angioplasty (PCTA) can widen a narrowing or occlusion of a blood vessel by dilation with a balloon.

Occasionally, angioplasty may be followed by an abrupt closure of the vessel or by a more gradual closure of the vessel, commonly known as restenosis. Restenosis refers to the renarrowing of the vascular lumen following vascular intervention, such as coronary artery balloon angioplasty with or without stent insertion. Restenosis is clinically defined as greater than 50% loss of initial luminal diameter gain following the procedure. Restenosis is believed to occur in about 30% to 60% of lesions treated by angioplasty and about 20% of lesions treated with stents within 3 to 6 months following the procedure. Acute closure may result from an elastic rebound of the vessel wall and/or by the deposition of blood platelets and fibrin along a damaged length of the newly opened blood vessel. In addition, restenosis may result from the natural healing reaction to the injury to the vessel wall (known as intimal hyperplasia), which can involve the migration and proliferation of medial smooth muscle cells that continues until the vessel is again occluded. To prevent such vessel occlusion, stents have been implanted within a body vessel. However, restenosis may still occur over the length of the stent and/or past the ends of the stent where the inward forces of the stenosis are unopposed.

To reduce the incidence of restenosis, one or more therapeutic agents, such as paclitaxel or other anti-restenotic agents, may be coated on the medical device. Paclitaxel is a compound which disrupts mitosis (M-phase) by binding to tubulin to form abnormal mitotic spindles or an analogue or derivative thereof. Such medical device coatings may be configured in various ways to release a therapeutic agent at a desired rate and over a desired time period upon implantation. Preferably, an implanted medical device releases a therapeutic agent at a point of treatment within a body vessel to promote a therapeutically desirable outcome, such as mitigation of restenosis.

For example, some medical device coatings include multi-layer coatings with separate layers having different-sized particles comprising the therapeutic agent. Published U.S. patent application US 2002/0082680 A1 by Shanley et al., filed Sep. 7, 2001, describes an expandable medical device having multiple layers comprising a beneficial agent stacked within an opening in a strut. Each layer may include particles of different sizes comprising the beneficial agent with differences in the particle sizes from layer to layer being selected to adjust the total drug flux eluting from the device as a function of the different particle sizes in each layer. Published U.S. patent application US 2005/0095267 A1 by Campbell et al., filed Dec. 3, 2003, describe implantable medical devices having nanoparticle drug coatings to improve the solubility of the drug. U.S. Pat. No. 5,873,313 to Ding et al., filed Jun. 13, 1996, describes spray coating of medical devices with microparticles of heparin using a pressurized airbrush.

Other medical device coatings adapted for controlled release of therapeutic agents such as paclitaxel rely on a polymer coating that is mixed with or applied over the releasable therapeutic agent to slow the release of the therapeutic agent from the medical device surface. For example, U.S. Pat. No. 6,589,546 to Kamath et al (filed Dec. 10, 2001) and Published US Patent Application 2004/0039441 by Rowland et al. (filed May 20, 2003) describe medical device coatings comprising a therapeutic agent mixed with a polymer to provide a controlled release of the therapeutic agent. Published US Patent Application 2003/0236513 by Schwarz et al. (filed Jun. 19, 2002) described medical device coatings comprising a polymer coating deposited over or mixed with a therapeutic agent to control the rate of release of the therapeutic agent from the device. U.S. Pat. No. 6,663,662 to Pacetti et al., filed Dec. 28, 2000, describes a multilayer medical device coating including a polymer diffusion barrier coating layer for reducing the elution rate of an underlying therapeutic substance. U.S. Pat. No. 6,770,729 to Van Antwerp, filed Sep. 30, 2002, discloses a medical device coating comprising a polymer mixed with a bioactive material to provide a controlled release of the bioactive material from the coating layer.

Typically, medical device coatings are configured to release a therapeutic agent at the same rate from all portions of the coating. However, for some clinical indications, adverse clinical indications, such as restenosis, may occur at only certain portions of the medical device surface. A therapeutic agent eluting device, such as a coated coronary stent, is typically selected to have a length at least equal to a length of an injured site (e.g., lesion) so as to extend the entire length of a lesion, preferably extending beyond the lesion. In some instances, restenosis may occur in tissue at or near the edges of the stent. This narrowing of the artery just beyond the edges of the stent is called the "edge effect." In patients experiencing the edge effect, a stented portion of a body vessel may remain free of significant restenosis, but portions of the body vessel at or beyond the edges of the stent may develop significant or even severe restenosis, requiring subsequent treatment. The severity of the restenosis at the edge and/or beyond edge areas is often greater at a portion of a body vessel proximal to the stent. The occurrence of edge effect may be attributable to uncovered diseased segments subjected to balloon trauma that are not covered by the stent, migration of smooth cells from the lesioned area, injury during the interventional procedure (e.g., balloon injury during angioplasty with or without the stenting), or the insufficient coverage of the original lesion. In the case of drug eluting stents, such effect may further be attributable to drastic gradient change between areas directly exposed to the drug and areas not directly exposed to the drug.

What is needed are medical devices that permit release of a therapeutic agent at a greater rate and/or a longer period of time from portions of the medical device coating that are prone to the edge effect. In particular, medical device coatings are needed that are capable of eluting a therapeutic agent at a different rate in at least two different regions of the abluminal surface of the device, with or without a polymer.

SUMMARY

Medical device coatings are provided that simultaneously release a therapeutic agent at different rates from different portions of the medical device coating. For example, preferred medical device coatings release a therapeutic agent more rapidly or for a longer duration in a first region of the abluminal surface than a second region of the abluminal surface. Preferred embodiments of the present invention provide a coated implantable medical device allowing for the release of a therapeutic agent into the adjacent or surrounding tissue at different rates at different regions of the medical device. Different elution rates of the therapeutic agent may be obtained by providing a coating with different-sized particles of the therapeutic agent on different portions of the device surface and/or applying a solution of the therapeutic agent with different liquid droplet sizes onto different portions of the medical device surface.

Preferably, the coating consists essentially of the therapeutic agent, and does not include a material, such as a polymer or non-polymer carrier, to modify the rate of release of the therapeutic agent. Coatings comprising up to 2% by weight of the coating of materials other than the therapeutic agent (such as polymers or other non-polymer carriers) are particularly preferred. Most preferably, the coatings comprise less than about 1.0 µg/mm² of materials other than the therapeutic agent that alter the release rate of the therapeutic agent from the coating. The therapeutic agent is preferably sparingly soluble in water. Agents suitable for administration to the wall of a body vessel, such as paclitaxel and paclitaxel derivatives, as well as rapamycin and rapamycin analogs, are particularly preferred therapeutic agents. The therapeutic agent is preferably a taxane therapeutic agent releasably coated on a portion of the medical device. The coated implantable medical devices may include a coating on one or more surfaces of the implantable device. Preferably, the coating comprising the therapeutic agent is present on the abluminal surface. Optionally, the coating may also be present on the luminal surface.

In a first embodiment, medical device coatings are provided that include particles comprising a therapeutic agent with two or more different particle sizes within a single layer on a surface of the implantable device. The coating may have a single-layer configuration having a first coating region including a plurality of first particles comprising the therapeutic agent and having a first average diameter, the first region extending from the distal end of the medical device to a second coating region; and a second coating region including a plurality of second particles comprising the therapeutic agent and having a second average diameter that is greater than the first diameter, the second region positioned distal to the first region along the length of the medical device. The smallest particles are preferably at least about 50% smaller than the largest particles. All of the particles are preferably uniformly distributed within each region, the first region having a smoother coating with a smaller total surface area compared to the second region due to the difference in average particle size between the two regions. The particles can have any suitable size and shape, but are preferably microparticles having an average diameter of about 1 to 100 micrometers, or smaller. The smaller particles typically release the therapeutic agent more quickly than the larger particles. Preferably, the smallest particles elute from the coating at least about 15% more quickly than the largest particles. More preferably, the coating is substantially free of a polymer or other substance besides the therapeutic agent.

In a second embodiment, medical device coatings are provided having a higher concentration of the therapeutic agent in a first region of the coating than in a second region of the coating. The coating may have any therapeutically effective amount of the therapeutic agent. Typically, the regions of the coating with the higher concentration of the therapeutic agent are configured to release the therapeutic agent more quickly. For example, regions of a coating with a higher concentration of the therapeutic agent preferably has a smaller average particle size than other regions of the coating with a lower concentration of the therapeutic agent. The concentration of the therapeutic agent may be measured in micrograms per square millimeter of the coating. The coating may include one or more therapeutic agent(s). Typical total concentrations of the therapeutic agent(s) in a coating are between about 0.5 and 5.0, preferably about 1.0-3.0, micrograms per square millimeter of coated abluminal surface area of an implantable vascular support frame, although higher concentrations (e.g., 9.0 µg/mm²) may also be desirable for some applications.

The implantable device may be configured as a radially-expandable vascular support frame having an abluminal surface and a luminal surface defining a substantially cylindrical lumen extending from a proximal end to a distal end. Portions of the coating on the abluminal surface of the implantable device proximate the distal and/or proximal ends preferably have a smaller particle size and a smoother surface morphology, while the coating between these regions preferably comprises larger particles and a rougher coating surface morphology. Typically, the regions of the coating with the smaller particles elute more quickly, permitting more rapid elution of the particulate therapeutic agent near the ends of the medical device and a comparatively slower elution rate from the larger particulate therapeutic agent in the central portion of the device. Optionally, the end portions of the coating may include a greater amount of the therapeutic agent (e.g., a thicker coating of smaller particles) than the central portion of the device. The more rapid elution rates and greater amount of therapeutic agent delivery from a coating near the ends of the medical device may be advantageous, for example, to mitigate the "edge effect."

In a third embodiment, medical device coatings are provided that are formed by certain coating processes. These coating processes preferably include applying a solution comprising a therapeutic agent and a suitable solvent to a surface of an implantable medical device. After contacting the solution with the surface of the device, the solvent can be removed to form a coating on the surface. Preferably, the coating is applied to the abluminal surface of a medical device configured as a vascular support frame by spraying the solution onto the surface. The solution is preferably sprayed onto a first region of the surface with a first average liquid droplet size and to a second region of the surface with a second average liquid droplet size that is greater than the first average liquid droplet size. The elution rates of the resulting coating may be varied by changing certain parameters of the spray applicator, such as an atomization gas pressure, during the spray coating process. Typically, the portions of the coating formed by spraying the solution at a higher atomization pressure comprise particles of the therapeutic agent with a smaller average size. Where the spray is uniformly sprayed over the surface of the medical device, regions of the coating with a smaller average particle size typically have a higher surface area, a lower surface roughness, and a higher rate of release of the therapeutic agent. Conversely, portions of the coating formed by spraying the solution at lower atomization pressures may include particles of the therapeutic agent having a larger size, forming a rougher coating with a lower surface area and a slower rate of release of the therapeutic agent. The first region is preferably positioned between the distal and/or proximal ends of the medical device and the second region. Preferably, both regions are portions of a single-layer coating consisting essentially of the therapeutic agent. Most preferably, the solution and the coating are substantially free of a polymer or other material besides the therapeutic agent.

In a fourth embodiment, methods of treatment are provided that include implanting a coated medical device. The medical device is preferably described in the first, second or third embodiments. A method of delivering a therapeutic agent to a peripheral blood vessel may include the steps of intralumenally inserting a coated vascular support frame into the blood vascular system using a means for intralumenal delivery comprising a catheter; positioning the coated medical device within a body vessel; and radially expanding the coated medical device within the body vessel so as to place at least a portion of the abluminal surface of the coated medical device in contact with a portion of a wall of the body vessel in a manner effective to deliver the therapeutic agent to the wall of the body vessel. The body vessel is preferably a peripheral artery, such as the femoral or iliac arteries. The coated medical device preferably includes an implantable structure having an abluminal surface and a luminal surface defining a substantially cylindrical lumen extending from a proximal end to a distal end and a particulate coating on the abluminal surface. The particulate coating may include at least a first coating region including a plurality of first particles comprising the therapeutic agent and having a first average diameter, the first region extending from the distal end to a second coating region and a second coating region including a plurality of second particles comprising the therapeutic agent and having a second average diameter that is greater than the first diameter, the second region positioned distal to the first region.

BRIEF DESCRIPTION OF THE DRAWINGS

FIG. 3 is a graph plotting hypothetical data points for the simultaneous release of a therapeutic agent from different regions of a coating at two different elution rates.

FIG. 4 is a schematic view of a method of spray coating the abluminal surface of an implantable medical device.

DETAILED DESCRIPTION

Definitions

Figure 1A:
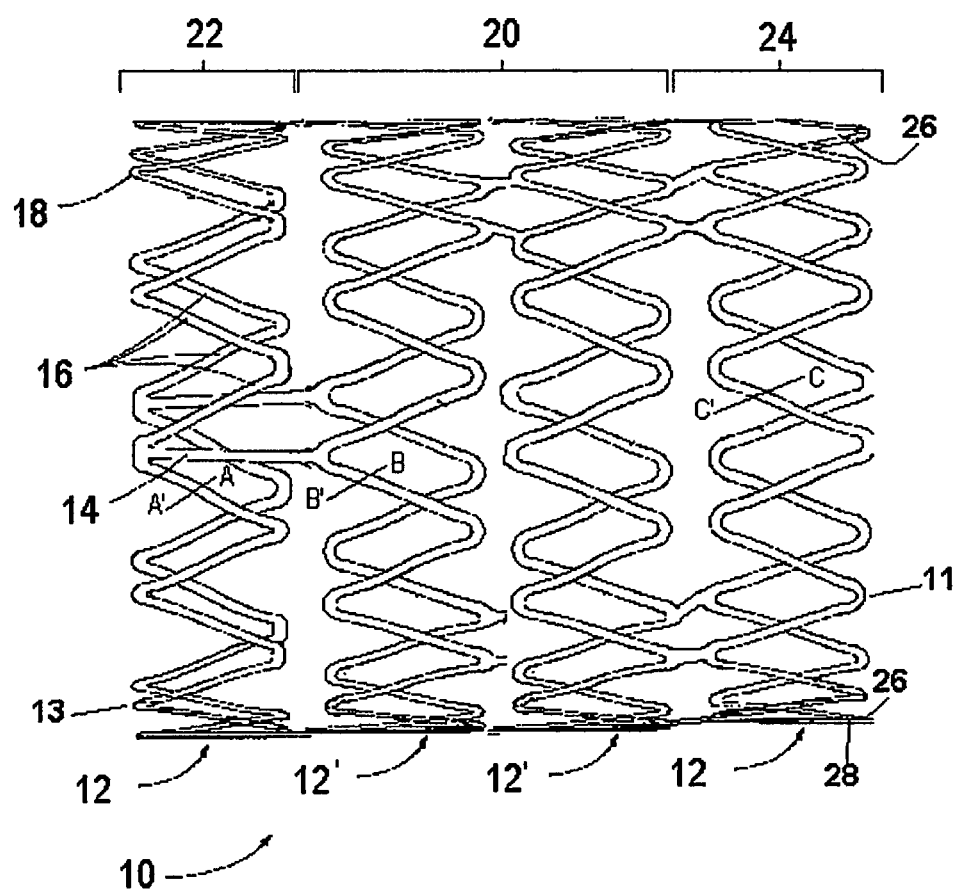
FIG. 1A is a side view of a coated implantable medical device configured as a radially-expandable vascular stent.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "hydrophobic," as used herein, refers to a substance with a solubility in water of less than 0.25 mg/mL at room temperature (about 25° C.).

The term "elution," as used herein, refers to removal of a material from a coating during contact with an elution medium. The elution medium can remove the material from the coating by any process, including by acting as a solvent with respect to the removable material. For example, in medical devices adapted for introduction to the vascular system, blood can act as an elution medium that dissolves a therapeutic agent releasably associated with a portion of the surface of the medical device. The removable material preferably includes the therapeutic agent. The therapeutic agent can be selected to have a desired solubility in a particular elution medium. Unless otherwise indicated, the term "release" referring to the removal of the therapeutic agent from a coating in contact with an elution medium is intended to be synonymous with the term "elution" as defined above. Similarly, an "elution profile" is intended to be synonymous with a "release profile," unless otherwise indicated.

An "elution medium," as used herein, refers to a set of physical conditions and/or fluid into which a therapeutic agent is released from a coating upon contact of the coating with the elution medium for a desired period of time. A suitable elution medium is any substance or environment into which the therapeutic agent can be released. The elution medium is desirably a fluid. More desirably, the elution medium is a biological fluid such as blood or porcine serum, although any other chemical substance can be used as an elution medium. For example, alternative elution media include phosphate buffered saline, blood, SDS, aqueous solutions, reaction conditions including temperature and/or pH, or combinations thereof, that release the therapeutic agent at a desired rate. Preferably, the elution medium is a fluid that provides an elution profile that is similar to the elution profile obtained upon implantation of the medical device within a body vessel. For example, porcine serum can provide an elution profile that is similar to the elution profile in blood for some coating configurations.

The term "effective amount" refers to an amount of a therapeutic agent sufficient to achieve a desired affect without causing an undesirable side effect. In some cases, it may be necessary to achieve a balance between obtaining a desired effect and limiting the severity of an undesired effect. It will be appreciated that the amount of therapeutic agent used will vary depending upon the type of active ingredient and the intended use of the composition of the present invention.

The term "luminal surface," as used herein, refers to the portion of the surface area of a medical device defining at least a portion of an interior lumen. Conversely, the term "abluminal surface," as used herein, refers to portions of the surface area of a medical device that do not define at least a portion of an interior lumen, such as the exterior surface. For example, where the medical device is a tubular frame formed from a plurality of interconnected struts and bends defining a cylindrical lumen the abluminal surface can include the exterior surface, sides and edges of the struts and bends, while the luminal surface can include the interior surface of the struts and bends.

The term "interface," as used herein, refers to a common boundary between two structural elements, such as two coating layers in contact with each other.

The term "coating," as used herein and unless otherwise indicated, refers generally to material attached to an implantable medical device. A coating can include material covering any portion of a medical device, and can be configured as one or more coating layers. A coating can have a substantially constant or a varied thickness and composition. Coatings can be adhered to any portion of a medical device surface, including the luminal surface, the abluminal surface, or any portions or combinations thereof.

The term "coating layer," as used herein, refers to a material of a given morphology or composition positioned over a substrate surface and oriented substantially parallel to the coated surface. A coating layer material can be positioned in contact with the substrate surface, or in contact with other material(s) between the substrate surface and the coating layer material. A coating layer can cover any portion of the surface of a substrate, including material positioned in separate discrete portions of the substrate or a continuous layer over an entire substrate surface. Separate coating layers include strata of particles of similar composition and morphology oriented parallel to a coated surface and differentiated by changes in the chemical composition of the coating and/or differences in the morphology of each layer (e.g., strata of different particle sizes positioned above or below one another).

The term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "alloy" refers to a substance composed of two or more metals or of a metal and a nonmetal intimately united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The terms "absorption," "bioresorption" and "bioabsorption" can be used interchangeably to refer to the ability of the polymer or its degradation products to be removed by biological events, such as by fluid transport away from the site of implantation or by cellular activity (e.g., phagocytosis). The term "bioabsorbable" will generally be used in the following description to encompass resorbable, absorbable, bioresorbable, and biodegradable.

A "biocompatible" material is a material that is compatible with living tissue or a living system by not being toxic or injurious.

A "non-bioabsorbable" or "biostable" material refers to a material, such as a polymer or copolymer, which remains in the body without substantial bioabsorption.

The phrase "controlled release" refers to an alteration of the rate of release of a therapeutic agent from a medical device coating in a given environment. A coating or configuration that alters the rate at which the therapeutic agent is released from a medical device provides for the controlled release of the therapeutic agent. The rate of a controlled release of a therapeutic agent may be constant or vary with time. A controlled release may be characterized by a drug elution profile, which shows the measured rate at which the therapeutic agent is removed from a drug-coated device in an elution medium as a function of time. A controlled release elution profile may include, for example, an initial burst release associated with the introduction of the medical device into the physiological environment, followed by a more gradual subsequent release. A controlled release can also be a gradient release in which the concentration of the therapeutic agent released varies over time or a steady state release in which the therapeutic agent is released in equal amounts over a certain period of time (with or without an initial burst release). A "sustained release" refers to prolonging the rate or duration of release of a therapeutic agent from a medical device.

As used herein, the phrase "therapeutic agent" refers to any implantable pharmaceutically active agent that results in an intended therapeutic effect on the body to treat or prevent conditions or diseases.

An "anti-proliferative" agent indicates any molecule that acts to inhibit cell proliferative events. Examples of anti-proliferative therapeutic agents include microtubule inhibitors such as vinblastine, vincristine, colchicine and paclitaxel, or derivatives thereof.

The term "pharmaceutically acceptable," as used herein, refers to those compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention.

When naming substances that can exist in multiple enantiomeric forms, reference to the name of the substance without an enantiomeric designation, such as (d) or (l), refers herein to the genus of substances including the (d) form, the (l) form and the racemic mixture (e.g., d,l), unless otherwise specified. For example, recitation of "poly(lactic acid)," unless otherwise indicated, refers to one or more compounds selected from the group consisting of: poly(L-lactic acid), poly(D-lactic acid) and poly(D,L-lactic acid). Similarly, generic reference to compounds that can exist in two or more polymorphs is understood to refer to the genus consisting of each individual polymorph species and any combinations or mixtures thereof.

As used herein, "derivative" refers to a chemically or biologically modified version of a chemical compound that is structurally similar to a parent compound and (actually or theoretically) derivable from that parent compound. A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115; Design of Prodrugs, H. Btndgaard (ed.), Elsevier, 1985; or H. Bundgaard, Drags of the Future 16 (1991) 443. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analog" or "analogue" refer to a chemical compound that is structurally similar to another but differs slightly in composition (as in the replacement of one atom by an atom of a different element or in the presence of a particular functional group), but may or may not be derivable from the parent compound. A "derivative" differs from an "analog" in that a parent compound may be the starting material to generate a "derivative," whereas the parent compound may not necessarily be used as the starting material to generate an "analogue."

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers.

Medical Device Coating Configurations

FIG. 1A shows a coated vascular support frame 10 comprising a tubular self-expanding vascular support frame having a luminal (interior) surface 26 defining a cylindrical lumen through the frame and an abluminal (outer) surface 28. Upon implantation of the vascular support frame 10 in a body vessel, the abluminal surface 28 contacts the interior wall of the body vessel. The vascular support frame 10 extends from a proximal end 11 to a distal end 13. The vascular support frame 10 has a tubular shape formed from a series of joined sinusoidal hoop members 12, 12' each formed from interconnected struts 16 and bends 18. Two end hoop members 12 are positioned at the distal end 13 and the proximal end 11, with one or more central hoop members 12 positioned between the end hoop members. A plurality of longitudinal struts 14 connect longitudinally adjacent hoop members 12, 12'. The longitudinal struts 14 are preferably straight and oriented substantially parallel to each other and parallel to a longitudinal axis 2 positioned in the center of the lumen defined by the vascular support frame 10.

Figure 1B:
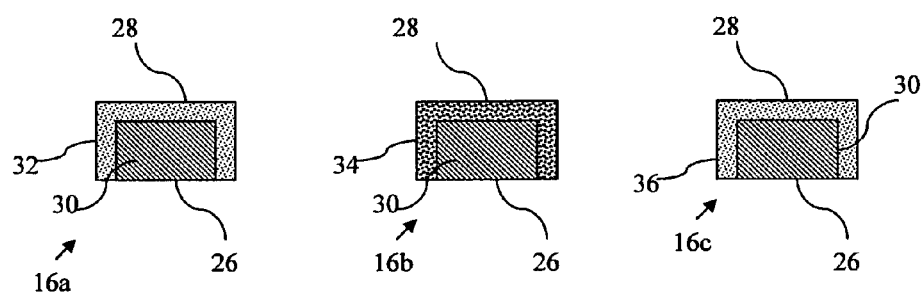
FIG. 1B is a series of cross sectional views of portions of the coated implantable medical device shown in FIG. 1A.

The vascular support frame 10 includes a coating 32 comprising a releasable therapeutic agent on the surface of the vascular support frame 10. The coating 32 may be applied to the luminal surface 26 and/or the abluminal surface 28 and may comprise one or more therapeutic agents. The coating 32 of the vascular support frame 10 is present on the abluminal surface 28. FIG. 1B shows a cross section of the coated vascular support frame 10 along line A-A' of a first coated strut 16a portion of an end hoop member 12 shown in FIG. 1A. Referring to FIG. 1B, the strut 16a can have any suitable cross sectional configuration, such as a rectangular cross section, and can be formed from any suitable material 30 such as a nickel titanium alloy, stainless steel or a cobalt chromium alloy. A coating 32 is present on the abluminal surface 28, and the two adjacent edges of the strut 16a. The coating 32 is not present on the luminal surface 26 of the strut 16a in the embodiment illustrated in FIG. 1A. Preferably, the coating 32 includes one or more particles of the therapeutic agents having a first average diameter that are released into an elution media (or within a body vessel) at a first rate. Preferably, the coating 32 is configured as a single-layer that provides zero-order kinetic elution from the coating.

FIG. 1B also shows a cross section of the coated vascular support frame 10 along line B-B' of a second coated strut 16b of a central hoop member 12' shown in FIG. 1A. Referring to FIG. 1D, the strut 16b is the same as the strut 16a, except as described below. The coating 32 present on the abluminal surface 28 of the strut 16b, and the two adjacent edges of the strut 16b, includes one or more particles comprising the therapeutic agent and having a second average diameter. The particles are released or dissolve within a body vessel (or into an elution media outside the body vessel) at a second rate. The second average particle diameter is preferably greater than the first average diameter of the particles in the coating on the first strut 16a of the end hoop member 12. More preferably, the surface area of the coating 32 over the first strut 16a is greater than the surface area of the coating on the second strut 16b. Importantly, the larger average diameter of the particulate therapeutic agent in the coating on the second strut 16b than the first strut 16a may provide a more rapid release of the therapeutic agent from the first strut 16a (and the coating on the end hoop members 12) into a body vessel or an elution medium outside a body, than the rate of simultaneous release of the therapeutic agent from the second strut 16b (and the coating on the central hoop members 12). While the coating 32 is discussed with respect to a single therapeutic agent, other embodiments provide for multiple therapeutic agents released from, or retained by, the coating 32. The release of the one or more therapeutic agents from the coating 32 may be altered by changing the particle size of therapeutic agents as a function of longitudinal position within a single layer on one or more surfaces of the vascular support frame 10. Preferably, the coating 32 includes smaller particles on the end hoop members 12, providing a more rapid release of the therapeutic agent, and larger particles on the central hoop members 12', providing a comparably slower rate of release of the therapeutic agent within a single-layer coating 32.

FIG. 1B further shows a cross section of a third strut 16c from the proximal end 11 hoop member 12 in FIG. 1A. The coating 32 is similar to that on the first strut 16a described above, and includes particles comprising the therapeutic agent and having a third average diameter that is less than the second average diameter of the particles of the coating 32 on the second strut 16*b*. The third average diameter may be less than, equal to, or greater than the first diameter of the particles on the first strut 16*a*. The rate of release of the therapeutic agent from the coating 32 on the third strut 16*c* (and the end hoop member 12) is preferably greater than the rate of release of the therapeutic agent from the second strut 16*b* (and the central hoop members 12), but may be equal to, less than or greater than the rate of release of the therapeutic agent from the first strut 16*a*.

Optionally, the coating 32 may also be present on the luminal surface 26 and be configured to retain a therapeutic agent, such as an antithrombogenic agent, positioned on the luminal surface 26 vessel. Alternatively, the coating 32 on the luminal surface 26 may be configured to release the therapeutic agent into fluid passing through the lumen of the vascular support frame 10 within the body vessel. The luminal surface 26 coating preferably retains an antithrombogenic therapeutic agent that inhibits or prevents thrombus formation within a body vessel, including anticoagulants, antiplatelets, and fibrinolytics.

The coating 32 is preferably a single layer consisting essentially of therapeutic agent particles of two or more average diameters. The particles are preferably substantially evenly distributed over an outer (e.g., abluminal) surface of a medical device to provide a first region having a smaller average particle size, higher surface area and smoother surface than a second region comprising a larger average particle size, a smaller surface area and a rougher surface. The regions of the coating having the smaller particle size typically release the therapeutic agent at a faster rate than coating regions having the larger average particle size. Referring again to FIG. 1A, the coating 32 preferably includes a first region 20 having particles with a first average diameter and a second region 22 having particles with a second average diameter that is less than the first average diameter. The first region 20 and the second region 22 are preferably contained within a single coating layer. Preferably, the coating particles are microparticles having a diameter of about 1-100 µm, or smaller. The smaller therapeutic agent coating particles in the first region 20 and a third region 24 may consist essentially of the therapeutic agent and have a first and a third diameter that is about 1-10 micrometer, while therapeutic agent coating particles in the second region 22 may have diameters of about 10-100 micrometers. Other embodiments provide coatings comprising nanoparticles having an average diameter of less than one micrometer, such as particle diameters of about 100 nanometer to 1 micrometer. Preferably, the largest particle diameter is at least 5% greater than the smallest diameter in a coating, more preferably at least 10%, 25%, 50%, 100%, 150%, 200%, 250%, 300%, 350%, 400%, 450% or 500% or greater than the smallest particle diameter. Particles with the smaller average diameter are preferably positioned in the distal or proximal region of the abluminal surface of the medical device. The coating 32 includes a third region 24 having particles with an average diameter that is smaller than the particles in the second region 20.

The roughness of the coating surface (i.e., maximum average peak-to-valley distances within a region of the coating) is typically greater in regions with higher average particle diameters if the particles are substantially evenly distributed over the entire surface. The surface roughness may be measured by any suitable technique, including Atomic Force Microscopy (AFM). Accordingly, the coating on the abluminal surface 28 may be rougher in the first region 20 than in the second region 22 or the third region 24.

The therapeutic agent particles in the coating preferably comprise or consist essentially of the therapeutic agent, which may be released upon implantation within a body vessel or contact with a suitable elution medium outside the body. The coating is preferably substantially free of materials other than the therapeutic agent, most preferably containing a total of less than 1 mg of materials other than a taxane therapeutic agent. For example, coatings preferably include less than about 5%, more preferably about 2%, by weight of materials, such as polymers or other non-polymer carriers, other than the therapeutic agent, that alter the release rate of the therapeutic agent. Coatings consisting essentially of the therapeutic agent include less than about 2% by coating weight of a material that alters the release rate of the therapeutic agent in the modified porcine serum elution medium prepared by adding 0.104 mL of a 6.0 g/L heparin solution to porcine serum at 37° C. and adjusting the pH to 5.6+/−0.3 using a 20% v/v aqueous solution of acetic acid. Most preferably, coatings include at least 95, 96%, 97%, 98%, 99%, or 99.5% by weight of the therapeutic agent. In addition, the coatings preferably comprise less than about 1.0 µg/mm$^2$ of materials other than the therapeutic agent that alter the release rate of the therapeutic agent from the coating. Most preferably, coatings comprise less than about 1.0, 0.9, 0.8, 0.8, 0.6, 0.5, 0.4, 0.3, 0.2 or 0.1 µg/mm$^2$ of materials other than the therapeutic agent. Most preferably, the coating and the particles are substantially free of a polymer. The coating may include a single layer consisting of the therapeutic agent, or consisting essentially of the therapeutic agent. Accordingly, the coating typically contains less than about 10 µg, or more preferably less than about 1, 0.50, 0.25, or 0.10 µg, of material other than the therapeutic agent (e.g., polymers or other carrier materials) per mm$^2$ of the total surface area of the medical device that is covered by the coating. Typically, the coating particles contain less than 0.10 µg of a polymer per mm$^2$ of the surface area of the medical device covered by the coating.

The thickness of the coating may be selected to provide a desired rate of release. The coating preferably has a thickness of about 0.1 µm to about 100 µm. The total thickness of the multi-layer coating on any given surface (e.g., luminal or abluminal) of the medical device is more preferably between about 0.2 µm and about 75 µm, preferably between about 0.4 µm and about 40, 50 or 60 micrometers. More preferably, the total thickness of the coating on the abluminal surface is between about 0.5 µm and about 50 µm. Most preferably, the coating consists essentially of a single layer of taxane therapeutic agent having a thickness of about 5-20 micrometers, typically about 10 micrometers. The coating may comprise a first region consisting essentially of particles of the therapeutic agent having a first average diameter and surface roughness proximate the distal and/or proximal regions of the abluminal surface, and having therapeutic agent particles of a second average diameter and surface roughness. The first average diameter is preferably less than the second average diameter, and the first surface roughness is preferably less than the second surface roughness. The therapeutic agent is preferably simultaneously released from the first region at a faster rate than from the second region. Also preferably, the first region includes a thicker coating (e.g., about 8-10 micrometers) with a higher total amount of therapeutic agent per square mm of coated surface area than the second region (e.g., about 5-7 micrometers).

Therapeutic Agents

The coating preferably comprises a therapeutically effective amount of one or more therapeutic agent(s) within a coating. The coating is preferably adapted to simultaneously release at least one of the therapeutic agents at two or more different rates from different regions of a single-layer of the coating. Optionally, portions of the coating may be configured to retain additional therapeutic agents. For example, a coating may include an abluminal coating adapted to release a first therapeutic agent at a first rate and a second rate from different regions of the abluminal surface of the coated medical device. In addition, the coating may also include a luminal coating adapted to retain a second therapeutic agent.

Preferably, the therapeutic agent is sparingly soluble or insoluble in water. For example, the therapeutic agent can be a hydrophobic compound, preferably having a solubility in water that is up to about 0.25 mg/mL, and more preferably less than about 0.20, 0.10, 0.05, 0.02 or 0.01 mg/mL water. The therapeutic agent may be provided in any suitable form, including a pharmaceutically acceptable salt, as a prodrug, or as a derivative or analog of a compound named herein, or equivalents thereto. The therapeutic agent can be selected to treat a desired clinical indication.

The therapeutic agent is preferably a taxane cell cycle inhibitor, such as paclitaxel, a paclitaxel analogue or paclitaxel derivative compound. Paclitaxel is a bioactive compound believed to disrupt mitosis (M-phase) by binding to tubulin to form abnormal mitotic spindles or an analogue or derivative thereof. Briefly, paclitaxel is a highly derivatized diterpenoid (Wani et al., J. Am. Chem. Soc. 93: 2325, 1971) which has been obtained from the harvested and dried bark of *Taxus brevifolia* (Pacific Yew) and Taxomyces Andreanae and Endophytic Fungus of the Pacific Yew (Stierle et al., Science 60: 214-216, 1993). The term "Paclitaxel" refers herein to a compound of the chemical structure shown as structure (1) below, consisting of a core structure with four fused rings ("core taxane structure," shaded in structure (1)), with several substituents.

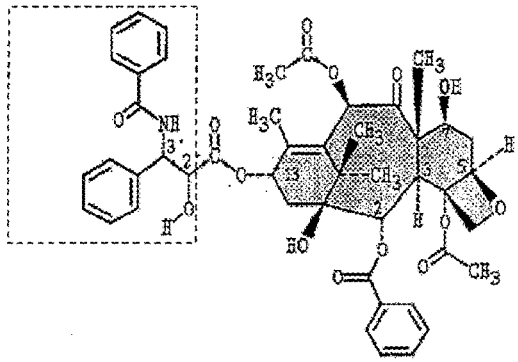

(1)

The therapeutic agent can be a taxane analog or derivative characterized by variation of the paclitaxel structure (1). Taxane therapeutic agents in general, and paclitaxel is particular, are considered to function as a cell cycle inhibitor by acting as an anti-microtubule agent, and more specifically as a stabilizer. Preferred taxane analogs and derivatives vary the substituents attached to the core taxane structure. In one embodiment, the therapeutic agent is a taxane analog or derivative including the core taxane structure (1) and the methyl-3-(benzamido)-2-hydroxy-3-phenylpropanoate moiety (shown in structure (2) below) at the 13-carbon position ("C13") of the core taxane structure (outlined with a dashed line in structure (1)).

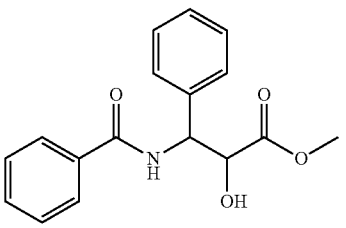

(2)

methyl 3-(benzamido)-2-hydroxy-3-phenylpropanoate

It is believed that structure (2) at the 13-carbon position of the core taxane structure plays a role in the biological activity of the molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-nitrophenyl)-N-dibenzoyl-N-(t-butoxycarbonyl)-10-deacetyltaxol.

A therapeutic agent composition comprising a taxane compound can include formulations, prodrugs, analogues and derivatives of paclitaxel such as, for example, TAXOL (Bristol Myers Squibb, New York, N.Y., TAXOTERE (Aventis Pharmaceuticals, France), docetaxel, 10-desacetyl analogues of paclitaxel and 3'N-desbenzoyl-3'N-t-butoxy carbonyl analogues of paclitaxel. Paclitaxel has a molecular weight of about 853 amu, and may be readily prepared utilizing techniques known to those skilled in the art (see, e.g., Schiff et al., Nature 277: 665-667, 1979; Long and Fairchild, Cancer Research 54: 4355-4361, 1994; Ringel and Horwitz, J. Nat'l Cancer Inst. 83 (4): 288-291, 1991; Pazdur et al., Cancer Treat. Rev. 19 (4): 351-386, 1993; Tetrahedron Letters 35 (52): 9709-9712, 1994; J. Med. Chem. 35: 4230-4237, 1992; J. Med. Chem. 34: 992-998, 1991; J. Natural Prod. 57 (10): 1404-1410, 1994; J. Natural Prod. 57 (11): 1580-1583, 1994; J. Am. Chem. Soc. 110: 6558-6560, 1988), or obtained from a variety of commercial sources, including for example, Sigma Chemical Co., St. Louis, Mo. (T7402—from *Taxus brevifolia*).

The therapeutically effective amount of the therapeutic agent(s) in the coating can depend upon the type and severity of the condition to be treated, the type and activity of the specific therapeutic agent employed, the method by which the medical device is administered to the patient; the age, body weight, general health, gender and diet of the patient, the time of administration, route of administration and rate of excretion of the specific compound employed, the duration of the treatment; and other appropriate factors considered in the medical arts. For example, a coating comprising a taxane therapeutic agent preferably includes up to about 10.0 µg of the taxane therapeutic agent per $mm^2$ of the coating, including 0.10-10.0 µg, as well as 0.01, 0.05, 0.10, 0.20, 0.25, 0.30, 0.40, 0.50, 0.60, 0.70, 0.75, 0.80, 0.90 1.00, 1.25, 1.50, 1.75, 2.00, 2.25, 2.50, 2.75, 3.00, 3.25, 3.50, 3.75, 4.00, 4.25, 4.50, 4.75 and 5.00 µg/$mm^2$ of the taxane therapeutic agent and intervals of about 0.01 and 0.001 therebetween. The coating preferably includes a single layer comprising between about 0.05-5.00 µg/$mm^2$, 0.50-5.00 µg/=$mm^2$, 1.00-5.00 µg/$mm^2$, 1.00-4.00 µg/$mm^2$, 1.00-3.00 µg/$mm^2$, and more preferably about 2.00-4.00 µg/$mm^2$, or most preferably about 3.00 µg/$mm^2$. The coating preferably includes a therapeutically effective total amount of the therapeutic agent. For coated vascular support frames for implantation in the coronary artery, coatings preferably include a total amount about 50-200 µg of a taxane therapeutic agent. For peripheral vascular coated implantable support frames preferably include a total amount about 100-1,000 μg of a taxane therapeutic agents, more preferably about 100-900 μg, and most preferably about 200-500 μg of the taxane therapeutic agent in the coating. For example, the coated medical device may be a 10×30 mm stent having an external diameter of about 7 French in the radially compressed state and an abluminal surface area of about 137 mm$^2$, coated with about 300-400 μg of paclitaxel to provide a coating with about 2.2-2.9 μg/mm$^2$ of paclitaxel.

Optionally, the coating may include one or more additional therapeutic agents selected to reduce incidence of thrombus formation on the surface of the medical device. For example, anticoagulants are therapeutic agents which act on any of the factors, cofactors, activated factors, or activated cofactors in the biochemical cascade and inhibit the synthesis of fibrin. Antiplatelet therapeutic agents inhibit the adhesion, activation, and aggregation of platelets, which are key components of thrombi and play an important role in thrombosis. Fibrinolytic therapeutic agents enhance the fibrinolytic cascade or otherwise aid in dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin. Further examples of antithrombotic therapeutic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalenyl-L-poly-L-arginyl, chloromethyl ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, antistreplase, reteplase, lanoteplase, monteplase, tenecteplase, urokinase, streptokinase, or phospholipid encapsulated microbubbles; and other therapeutic agents such as endothelial progenitor cells or endothelial cells.

Therapeutic Agent Elution Profile

The amount of therapeutic agent in the coating can be measured by dissolving the coating in a suitable elution medium and measuring the concentration of the therapeutic agent in the elution medium. An elution medium can be selected to solubilize the therapeutic agent sufficiently rapidly, while allowing for subsequent measurement of the solubilized therapeutic agent in a manner that can be correlated to the amount of the therapeutic agent that was in the medical device coating. Examples of suitable elution media for a taxane therapeutic agent include ethanol, aqueous cyclodextrin solutions (e.g., an aqueous solution of Heptakis-(2,6-di-O-methyl)-β-cyclodextrin (HCD)), phosphate buffered saline (PBS), bovine serum albumin (BSA) and sodium dodecyl sulfate (SDS).

The therapeutic agent can be identified in the elution media by any suitable method, such as UV-spectrophotometry. Suitable detection methods, such as a spectrographic technique, permit measurement of a property of the elution medium that can be correlated to the presence or concentration of the taxane therapeutic agent with a desired level of accuracy and precision. For example, the core taxane structure can be identified from an ultraviolet (UV) spectrum of the taxane therapeutic agent in any suitable solvent that permits measurement of a characteristic peak of the taxane therapeutic agent in solution. In one embodiment, absorption spectroscopy can be used to detect the presence of a taxane therapeutic agent in an elution medium. Accordingly, the Beer-Lambert Correlation may be used to determine the concentration of a taxane therapeutic agent in a solution. This correlation involves determining the linear relationship between absorbance and concentration of an absorbing species (the taxane therapeutic agent in the elution medium). Using a set of standard samples with known concentrations, the correlation can be used to measure the absorbance of the sample. A plot of concentration versus absorbance can then be used to determine the concentration of an unknown solution from its absorbance. Ethanol is a preferred example of a suitable solvent. Paclitaxel provides a characteristic peak at 227 nm indicative of the presence of the core taxane structure of paclitaxel in the solution. The taxane therapeutic agent in an ethanol elution medium provides a UV spectrum comprising the characteristic peak at about 227 nm that can be correlated to the presence of the taxane therapeutic agent in the solution. The following parameters may be used to correlate the UV spectra measurements to paclitaxel concentration:

Beer's Law: $A=\epsilon lc$
$A=O.D._{max}$ at 227 nm
$c=[PTX]M$
$l=1$ cm
$\epsilon=$extinction coefficient($cm^{-1} \cdot M^{-1}$)
(29,500 for EtOH; 28,900 for 0.5% aqueous HCD)

In addition, the rate of elution of the therapeutic agent from the coating can be described by a release profile. The elution profile of a medical device comprising a therapeutic agent shows the percentage of the therapeutic agent that dissolves as a function of time in a given environment. The rate of dissolution of the therapeutic agent can vary based on the solvent being used and the solid form of the therapeutic agent before dissolution. An elution profile can be obtained by any suitable method that allows for measurement of the release of the therapeutic agent in a manner that can be measured with a desired level of accuracy and precision. In one embodiment, the elution profile of the release of a taxane therapeutic agent is obtained by contacting the medical device with a suitable elution medium. The elution medium can be formulated to simulate conditions present at a particular point of treatment within a body vessel. For example, an elution medium comprising porcine serum can be used to simulate implantation within a blood vessel. The release of taxane therapeutic agent from the medical device can be measured by any suitable spectrographic method, such as measurement of a UV absorption spectrum of the test fluid after contacting the medical device.

Figure 2:
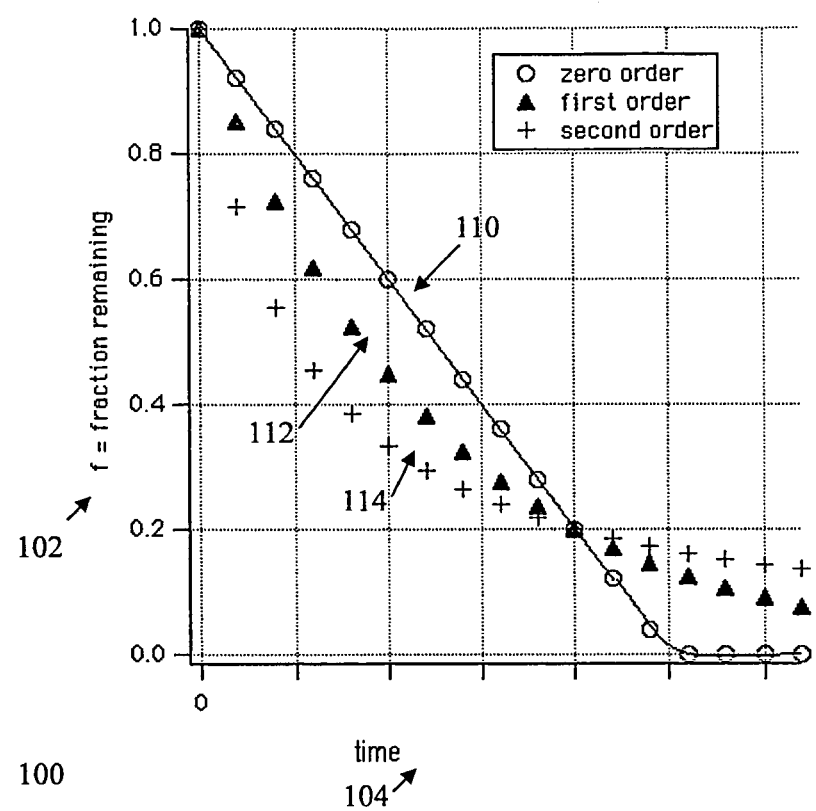
FIG. 2 is a graph plotting hypothetical data points for different elution profiles of a therapeutic agent from a coated medical device.
Figure 5A:
FIGS. 5A and 5B are optical micrographs showing spray coating droplets on a mandrel during the spray coating process depicted in FIG. 4.
Figure 5B:
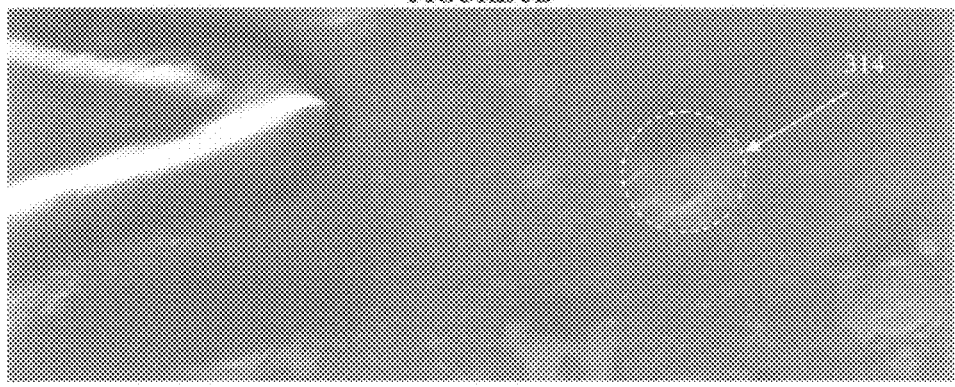

By monitoring the concentration of the therapeutic agent in an elution medium in contact with the coating, the rate of release of the therapeutic agent from the coating can be measured as a function of time. The kinetics of the rate of release of the therapeutic agent can depend on the size of the particles of therapeutic agent in the coating layer. Preferably, the coating is configured to release the therapeutic agent with zero-order or first-order kinetics. First-order release kinetics of a therapeutic agent from an abluminal surface provides an immediate release of the therapeutic agent into local tissue, followed by a gradual decline. Zero-order kinetic release provides a slow release of the therapeutic agent over a sustained time with steady tissue concentrations of the drug. FIG. 2 shows a graph 100 of hypothetical data points for a percent release of a therapeutic agent 102 versus time 104 for a theoretical elution of the therapeutic agent according to a zero-order kinetic release 110, a first order kinetic release 112 and a second order kinetic release 114. A plot of the natural log (ln) of the fraction of therapeutic agent remaining against time would provide a straight line for the first order kinetics (not shown), and a plot of the reciprocal of the fraction remaining (1/f) against time would provide a straight line for second order kinetics (not shown).

The elution rate of the therapeutic agent can vary at different portions of a single layer coating. Referring to the coated vascular support frame 10 in FIG. 1A, a portion of the coating 32 in the central region 20 with a larger average particle size can elute at a slower rate than the coating 32 in the distal region 22 or the proximal region 24 with a smaller average particle size than the central region 20. For a given coating volume, smaller particle sizes can increase the total particle surface area in the coating. The total elution rate of the therapeutic agent can be altered between regions of a single-layer coating, providing elution kinetics that vary depending on the particle size. FIG. 3 shows a graph 120 of hypothetical data points showing a fraction of therapeutic agent remaining in the coating 122 in contact with an elution medium as a function of time 124 of contact between the elution medium and time. A first idealized first zero-order release rate 132 may be obtained from the release of the therapeutic agent from the first region 22 and the third region 24. A second idealized second zero-order release rate 130 may be obtained from the release of the therapeutic agent from the second region 20. Accordingly, the therapeutic agent may be locally delivered to the inner wall of the body vessel proximate to the proximal end 11 and the distal end 13 of the coated vascular support frame 10.

Medical Devices

While certain preferred embodiments relating to a coated vascular support frame are described herein, the coatings may be applied to any implantable medical device. The coated medical device may be any device that is adapted for introduction temporarily or permanently into the body for the prophylaxis or therapy of a medical condition. For example, such medical devices may include, but are not limited to, stents, stent grafts, vascular grafts, catheters, guide wires, balloons, filters (e.g. vena cava filters), cerebral aneurysm filler coils, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves (e.g. venous valves), abdominal aortic aneurysm (AAA) grafts, embolic coils, various types of dressings, bone substitutes, intraluminal devices, vascular supports, or other known bio-compatible devices.

In general, endoluminally-implantable vascular support frames typically comprise a plurality of interconnected struts and bends defining apertures or open spaces therebetween. The struts and bends may form a plurality of sinusoidal hoop members longitudinally aligned to form a cylindrical structure. Vascular support frames may have other configurations, such as braided tubes or interconnected helical flexible members. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of intraluminal vascular support frames include endovascular, biliary, tracheal, gastrointestinal, urethral, ureteral, esophageal and coronary vascular support frames. The intraluminal vascular support frames may be, for example, balloon-expandable or self-expandable.

In one embodiment, the medical device comprises an intraluminal vascular support frame configured as a self-expanding or balloon-expandable device. The device may be a bifurcated stent, a coronary vascular support frame, a urethral stent, a ureteral stent, a biliary stent, a tracheal stent, a gastrointestinal stent, or an esophageal stent, for example. The vascular support frame or other medical device may be made of one or more suitable biocompatible materials such as stainless steel, nitinol, NP35N, gold, tantalum, platinum or platinum irdium, niobium, tungsten, iconel, ceramic, nickel, titanium, stainless steel/titanium composite, cobalt, chromium, cobalt/chromium alloys, magnesium, aluminum, or other biocompatible metals and/or composites or alloys. Desirably, the device is made of stainless steel, cobalt-chromium or nitinol.

The coated implantable medical device is preferably configured as a radially-expandable cylindrical vascular support frame having an abluminal (exterior) surface and a luminal surface defining a substantially tubular lumen extending axially through the device. Preferably, the support frame is radially-expandable from a compressed delivery configuration to a radially-expanded configuration with a larger diameter. For example, the support frame may be crimped to a compressed diameter suitable for delivery from a catheter having a suitable diameter for intraluminal delivery within a blood vessel (e.g., 5-10 French, preferably about 5-7 French for implantable vascular support frames, including increments of about 0.1 French therebetween). The radially-expanded configuration may have a diameter suitable for maintaining patency of a body vessel, such as 2-20 mm, including increments of about 0.1 mm therebetween. Typically, vascular support frames are formed by a plurality of interconnected resilient sinusoidal hoop members. The vascular support frame may be self-expanding or balloon expandable, depending on the frame material. The vascular support frame may include a plurality of openings between the abluminal and luminal surfaces. Preferably, the coating is applied to the abluminal surface. More preferably, the coating is not applied to the luminal surface. The coated implantable medical device coating may be configured to release a therapeutic agent adhered to a surface of the medical device over a desired period of time. Preferably, the medical device is a radially-expandable vascular support frame, such as the Zilver® product sold by Cook Incorporated (Bloomington, Ind.).

Methods of Coating

In a second embodiment, methods of coating a medical device are provided, as well as coated medical devices formed according to these methods. The therapeutic agent coatings are preferably deposited by spraying a therapeutic agent solution comprising or consisting of the therapeutic agent and a suitable solvent onto the surface of a medical device. Preferably, the therapeutic agent is deposited on the medical device surface as a coating layer having two or more different elution rates within the layer by changing the spray coating parameters during the spray coating process. In particular, varying the air or liquid pressure during the spray coating process can alter the rates at which the coated therapeutic agent elutes from different regions of the coating. For example, a single-layer coating may include a first region with a therapeutic agent that dissolves at a first rate upon implantation and a second region that elutes at a second rate that is slower than the first rate. Where the medical device is a vascular support frame, the first region may be disposed on the distal and/or proximal portions of the abluminal surface and the second region may be centrally disposed between the distal and proximal regions.

Preferably, the methods of spray coating the therapeutic agent solution deposit particles of various sizes comprising or consisting of the therapeutic agent. For example, the first region of a coating may be formed as particles consisting of the therapeutic agent having a first average diameter, while the second region of the coating may include particles consisting of the therapeutic agent having a second average diameter that is greater than the first diameter. The coating preferably includes an approximately uniform spatial distribution of the particles over the abluminal surface of the medical device. Accordingly, a region comprising smaller particles, a higher surface area and a more rapid elution rate may have a smoother surface than another region comprising larger particles, a lower surface area and a slower elution rate.

An exemplary spray coating method embodiment is illustrated in FIG. 4. A medical device configured as a cylindrical radially-expandable vascular support frame 210 is placed over a mandrel 240 to form a mounted stent assembly 210'. A therapeutic agent solution 232 is contained within a tank reservoir 230. The therapeutic agent solution 232 typically comprises the therapeutic agent dissolved in a solvent that evaporates during the spray coating process, to leave sufficient amounts of the therapeutic agent deposited on a surface of a medical device, preferably as solid particles consisting essentially of the therapeutic agent. Any suitable concentration of therapeutic agent in a solvent may be used. For example, the solution 232 can be made with any suitable concentration of the taxane therapeutic agent and ethanol. Solutions of about 1-10 g of a taxane therapeutic agent per liter of ethanol are preferred. Also preferred are solutions of 0.5-5 M paclitaxel or paclitaxel derivative in ethanol, with a solution of about 2-4 M being particularly preferred. Alternatively, the solution 232 may include one or more solvents, such as methanol, water, ethanol, dichloromethane, or combinations thereof. Varying the ratio of two or more solvents in the spray solution 232 may change the elution rate of the resulting coating 32 layer that is deposited. Generally, increasing the amount of water in a spray solution 232 comprising water, methanol and paclitaxel results in a coating layer with a slower elution rate of paclitaxel. Preferably, the therapeutic agent solution is substantially free of a polymer or material other than the therapeutic agent and the solvent(s). In particular, solutions with concentrations of less than about 0.1 mM of materials other than the therapeutic agent(s) and the solvent(s) are preferred.

The therapeutic agent solution 232 is applied to the abluminal surface of the vascular support frame 210 with a spray applicator 220. The spray applicator 220 is preferably an EFD spray valve, although any suitable device providing for the application of the therapeutic agent solution 232 as a fine spray of micrometer-sized droplets may be used. The spray applicator 220 preferably provides a pressurized spray plume 250 of the therapeutic agent solution 232 as a fine mist comprising liquid droplets having diameters that are on the order of micrometers or nanometers. More preferably, the spray applicator 220 permits the variation of the size and distribution of liquid droplets within the spray plume 250 as a function of parameters, such as liquid pressure in the reservoir 230 or atomization pressure within the spray applicator 220, that are readily adjusted while spraying the therapeutic agent solution 232 onto the vascular support frame assembly 210'.

Referring to the coating apparatus in FIG. 4, a pressure line 234 provides a liquid tank pressure to the reservoir 230, driving therapeutic agent solution 232 through the solution conduit 228 to the spray applicator 220, such as an EFD780 series spray dispense valve (EFD, East Providence, R.I.). An atomization air conduit 224 provides pulsed pressurized air for atomization of the therapeutic agent solution 232. A second conduit 226 provides pulsed pressurized air for valve operation. The pressurized air in the second conduit is provided at any suitable pressure, such as about 70 psi. In operation, pulsed air from the second conduit 226 acts as a piston that retracts a needle from a nozzle seat, allowing the therapeutic agent solution 232 to flow from a nozzle 222. Nozzle air from the atomization air conduit 224 flows from an annulus around the liquid nozzle, creating a pressure drop around the nozzle 222 that causes the therapeutic agent solution 232 from the solution conduit 228 to atomize into fine liquid droplets in a spray plume 250. The atomization pressure may be selected to provide a desired coating morphology and/or spray plume 250 droplet size. Typically, an atomization pressure can be selected between about 1 and 30 psi. The rate of spray and area of spray are controlled by the timing of the valve open time, reservoir pressure and the nozzle size and distance 256 from the vascular support frame assembly 210'.

The position 254 of the nozzle 222 and the vascular support frame assembly 210' may be varied to provide a desired spray density and particle size in the spray plume 250. Alignment of the spray applicator 220 and vascular support frame 230 may be performed with the use of a laser beam, which may be used as a guide when passing the spray gun over the medical device(s) being coated. The distance between the spray nozzle 222 and the nozzle size can be selected depending on parameters apparent to one of ordinary skill in the art, including the area being coated, the desired thickness of the coating and the rate of deposition. Any suitable distance and nozzle size can be selected. For example, for coating an 80 mm long vascular support frame 230, a distance of between about 1-10 inches (preferably, about 5-8 inches) between the nozzle 222 and vascular support frame 230 is preferred, depending on the size of the spray pattern desired. The nozzle 222 diameter can be, for example, between about 0.014-inch to about 0.046-inch.

Figure 6A:
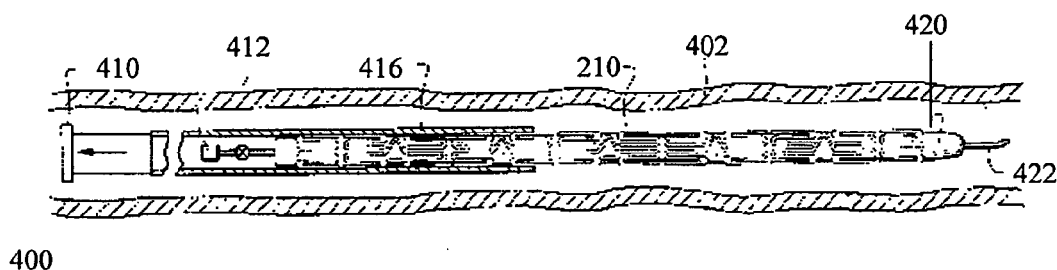
FIGS. 6A-6C are schematic views of a method of implanting a coated medical device within a body vessel by balloon expansion of the coated medical device.
Figure 6B:
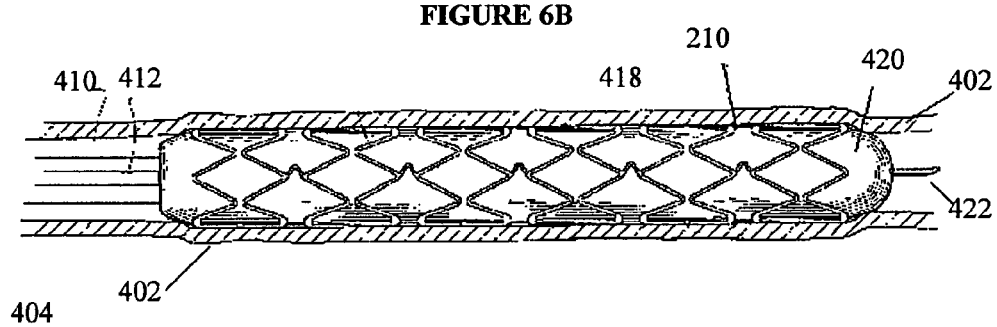
Figure 6C:
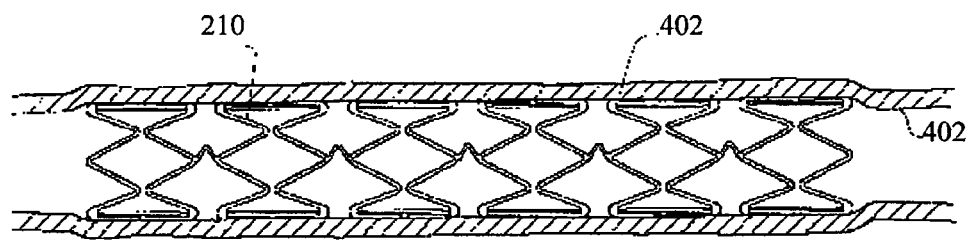

The elution rate of the therapeutic agent in the resulting spray coating is preferably controlled by varying certain parameters of the spray coating process. Preferably, the nozzle is passed over the surface of the vascular support frame 210 while spraying. The vascular support frame assembly 210' may be rotated along the longitudinal axis as the nozzle 222 is longitudinally translated one or more times between a distal end 212a to a proximal end 216b. Spray coating parameters such as the pressure in the pressure line 234 and/or the solution conduit 228 (liquid pressure) and/or the atomization pressure in the atomization air conduit 224 can be varied while the nozzle 222 is passed over different regions of the vascular support frame 230 abluminal surface. For example, a spray plume 250 produced using a first atomization pressure in the atomization air conduit 224 can be contacted with a first region 212 of the vascular support frame 230. The atomization pressure in the atomization air conduit 224 may then be increased while the spray plume 250 contacts a second region 214, producing a therapeutic agent coating in the second region 214 that will elute at a different rate than the coating in the first region 212. Similarly, the atomization pressure in the atomization air conduit 224 may be decreased when the spray plume contacts a third region 216 at the proximal end of the vascular support frame 230, to produce a coating that will elute at a different rate than the coating in the second region 214. Typically, decreasing the atomization pressure in the atomization air conduit 224 will result in a coating that releases the therapeutic agent more rapidly in an elution medium. For example, the first region 212 and the third region 216 may be coated with a paclitaxel-ethanol solution at an atomization pressure of about 10-15 psi (preferably about 13 psi), and the second region 214 may be coated at an atomization pressure of about 20-30 psi (preferably about 25 psi) to produce a coated vascular support frame 230 that elutes paclitaxel more rapidly from the distal and proximal ends (regions 212, 216, respectively) than in the center (region 214). Preferably, the spraying step is performed at a temperature of between about 65° F. and 75° F.

One or more regions of the medical device surface may be coated with a larger amount of the therapeutic agent. For example, the first region 212 may have a higher dose of the therapeutic agent per unit area than the second region 214. A higher dose of the therapeutic agent may be provided by contacting a region of the surface coating with the spray plume 250 for a longer period of time than another region. For example, more therapeutic agent may be applied to the first region 212 than the second region 214 by one or more of the following techniques: the spray plume 250 may be translated over the first region 212 more times than the second region 214, the spray plume 250 may be moved more slowly over the first region 212 than the second region 214, multiple spray plumes 250 may be used to coat the first region 212 but not the second region 214 and/or a higher concentration of the therapeutic agent in the therapeutic agent solution 232 may be used to coat the first region 212 compared to the second region 214. Preferably, the first region 212 and the third region 216 have a coating comprising about 3-10 micrograms of a taxane therapeutic agent per square mm of coated abluminal surface area in these regions, and the second region 214 has a coating comprising about 1-2 micrograms of the taxane therapeutic agent per square mm of the coated abluminal surface area in this region.

In one aspect of the second embodiment, a coated implantable medical device having an abluminal surface and a luminal surface defining a substantially cylindrical lumen extending from a proximal end to a distal end is formed by the steps of: applying a solution comprising a volatile solvent and a therapeutic agent with a first average liquid droplet size onto a first region of the abluminal surface of the implantable structure extending from the distal end of the implantable structure; and applying the solution with a second average liquid droplet size greater than the first average liquid droplet size onto a second region of the abluminal surface of the implantable structure positioned proximal to the first region of the implantable structure to form a coating. FIG. 5A is an optical micrograph of a first region of a vascular support frame assembly 230' after spray coating at a first atomization pressure of about 25 psi, before evaporation of the solvent, showing a first droplet 312 having a first diameter. FIG. 5B is an optical micrograph of a second region of the vascular support frame assembly 230' after spray coating at a second atomization pressure of about 13 psi, before evaporation of the solvent, showing a second droplet 314 having a second diameter that is larger than the first diameter of the first droplet 312. A portion of the vascular support frame 230 is shown in both FIG. 5A and FIG. 5B, which are of comparable scale.

In another aspect of the second embodiment, a coated implantable medical device having an abluminal surface and a luminal surface defining a substantially cylindrical lumen extending from a proximal end to a distal end is formed by the steps of: applying the solution onto a first region of the abluminal surface of the implantable structure extending from the distal end of the implantable structure to form a particulate coating having a first average diameter; and applying the solution onto a second region of the abluminal surface of the implantable structure positioned proximal to the first region of the implantable structure to form a particulate coating in the second region having a second average diameter that is greater than the first average diameter.

Methods of Treatment

In a third embodiment, methods of treating various conditions are described, preferably comprising the implantation of a coated medical device according to the first embodiment and/or coated medical devices prepared according to the methods of the second embodiment. A method of treatment typically involves inserting a coated medical device into a patient. For example, when the medical device is a coated stent, the method of treatment involves implanting the stent into the vascular system of a patient and allowing the therapeutic agent(s) to be released from the stent. In a first aspect of the third embodiment, the coating includes a first region having particles of the therapeutic agent with a first average diameter, and a second region having particles of the therapeutic agent with a second average diameter that is larger than the first diameter. In a second aspect of the third embodiment, the coating includes a first region applied by spray coating a solution of the therapeutic agent and a volatile solvent with a first atomization pressure, and a second region applied by spray coating the solution at a second atomization pressure that is greater or less than the first atomization pressure. Preferably, the solution does not contain a polymer or other materials besides the therapeutic agent and the solvent(s). The solvent is preferably evaporated during or after contacting the abluminal surface of the medical device with the sprayed solution to form a coating comprising particles that include the therapeutic agent. Preferably, the coating consists essentially of particles that consist essentially of the therapeutic agent.

FIGS. 6A-6C show the endovascular implantation of a coated medical device 210 within a body vessel 402 from a delivery catheter 410 positioned within the body vessel 402. The coated medical device 210 in FIGS. 6A-6C is a balloon-expandable vascular support frame formed from a series of six longitudinally-connected sinusoidal hoop members radially compressed around a catheter balloon 420 for delivery. As shown in FIG. 6A, a delivery catheter 410 is positioned at a site of treatment within a body vessel 402 along a guidewire 422 in a first step 400. For example, for implantation in a body vessel 402 such as the superficial artery, popliteal artery or tibial artery, support frame 210 designs with increased resistance to crush may be desired. For implantation in the renal or iliac arteries, frame designs with suitable levels of radial force and flexibility may be desired. Preferably, a coated vascular support frame is implanted in a non-coronary peripheral artery, such as the iliac or renal arteries. The coated medical device 210 is a radially-expandable cylindrical vascular support frame 210 having a therapeutic agent coated on the abluminal surface. The vascular support frame 210 can be selected based on the desired site of implantation, and may be self-expanding or balloon-expandable.

The delivery catheter 410 may optionally include a retractable protective sheath 416 that can be translated in the proximal direction, away from the distal end of the catheter 410, relative to the radially compressed vascular support frame 230. As shown in a second step 404 in FIG. 6B, the balloon 420 may be inflated through an inflation lumen 412 running through the shaft of the catheter 410. The balloon 420 is inflated, until the abluminal surface coating of the vascular support frame 210 contacts the inner wall of the body vessel 402 and the vascular support frame 210 is secured within the body vessel 402. Preferably, the distal and proximal ends of the abluminal surface of the vascular support frame include a coating that releases the therapeutic agent more rapidly into the inner wall of the body vessel 402 than the center portion of the abluminal surface, thereby reducing the edge effect upon implantation. After implantation of the vascular support frame 210, the balloon 420 can be deflated and the catheter 410 removed from the body vessel in a third step 408, leaving the vascular support frame 210 in place (as shown in FIG. 6C).

In one embodiment, a medical device comprising a radially-expandable frame portion coated with a therapeutic agent can be endoluminally delivered to a point of treatment within an infrapopliteal artery, such as the tibial or peroneal artery or in the iliac artery, to treat CLI. For treating focal disease conditions, coated balloon-expandable medical devices can comprise an expandable frame attached to a coating. The frame can also be formed from a bioabsorbable material, or may optionally include a barb or other means of securing the medical device to the wall of a body vessel upon implantation.

In another embodiment, a coated medical device can be a self-expanding device such as a coated Nitinol support frame configured to provide a desirable amount of outward radial force to secure the medical device within the body vessel. The medical device can be preferably implanted within the tibial arteries for treatment of CLI. For instance, the coated medical device can be configured as a vascular support frame having a self-expanding support frame formed from a superelastic self-expanding nickel-titanium alloy coated with a metallic bioabsorbable material and attached to a graft material. A self-expanding frame can be used when the body vessel to be stented extends into the distal popliteal segment. The selection of the type of implantable frame can also be informed by the possibility of external compression of an implant site within a body vessel during flexion of the leg.

The methods for delivering a medical device are also applicable to treatment of any suitable body vessel, such as a vein, artery, biliary duct, ureteral vessel, body passage or portion of the alimentary canal. Sites for placement of the medical devices include sites where local delivery of taxane therapeutic agents are desired. Common placement sites include the coronary and peripheral vasculature (collectively referred to herein as the vasculature). Other potential placement sites include the heart, esophagus, trachea, colon, gastrointestinal tract, biliary tract, urinary tract, bladder, prostate, brain and surgical sites, particularly for treatment proximate to tumors or cancer cells. Where the medical device is inserted into the vasculature, for example, the therapeutic agent may be released to a blood vessel wall adjacent the device, and may also be released to downstream vascular tissue as well.

In one preferred embodiment, the coated medical devices are implanted to treat peripheral vascular disease, for example by implanting the coated medical device in a peripheral artery. Peripheral vascular disease (PVD) is a common condition with variable morbidity affecting mostly men and women older than 50 years. Peripheral vascular disease of the lower extremities comprise a clinical spectrum that goes from asymptomatic patients, to patients with chronic critical limb ischemia (CLI) that might result in amputation and limb loss. Critical limb ischemia is a persistent and relentless problem that severely impairs the patient functional status and quality of life, and is associated with an increased cardiovascular mortality and morbidity. It can present acutely (i.e. distal embolization, external compression, acute thrombosis, etc.) or, in the majority of cases, as chronic CLI. Based on incidence rates extrapolated to today's increasingly aging population, PVD affects as many as 10 million people in the United States (Becker G J, McClenny T E, Kovacs M E, et al., "The importance of increasing public and physician awareness of peripheral arterial disease," J Vasc Interv Radiol., 13(1):7-11 (January 2002)). As the population ages, the family physician will be faced with increasing numbers of patients complaining of symptoms of lower extremity PVD. Nearly one in four of the approximately 60,000 people screened annually through Legs for Life, a nationwide screening program, are determined to be at moderate to high risk of lower extremity PVD and are referred to their primary care physicians for diagnosis (data collected by the Society of Cardiovascular and Interventional Radiology) (Becker G J, McClenny T E, Kovacs M E, et al., "The importance of increasing public and physician awareness of peripheral arterial disease," J Vasc Interv Radiol., 13(1):7-11 (January 2002)).

Chronic critical limb ischemia (CLI) is defined not only by the clinical presentation but also by an objective measurement of impaired blood flow. Criteria for CLI diagnosis include either one of the following (1) more than two weeks of recurrent foot pain at rest that requires regular use of analgesics and is associated with an ankle systolic pressure of 50 mm Hg or less, or a toe systolic pressure of 30 mm Hg or less, or (2) a nonhealing wound or gangrene of the foot or toes, with similar hemodynamic measurements. The hemodynamic parameters may be less reliable in patients with diabetes because arterial wall calcification can impair compression by a blood pressure cuff and produce systolic pressure measurements that are greater than the actual levels. Ischemic rest pain is classically described as a burning pain in the ball of the foot and toes that is worse at night when the patient is in bed. The pain is exacerbated by the recumbent position because of the loss of gravity-assisted flow to the foot. Ischemic rest pain is located in the foot, where tissue is farthest from the heart and distal to the arterial occlusions. Patients with ischemic rest pain often need to dangle their legs over the side of the bed or sleep in a recliner to regain gravity-augmented blood flow and relieve the pain. Patients who keep their legs in a dependent position for comfort often present with considerable edema of the feet and ankles. Nonhealing wounds are usually found in areas of foot trauma caused by improperly fitting shoes or an injury. A wound is generally considered to be nonhealing if it fails to respond to a four- to 12-week trial of conservative therapy such as regular dressing changes, avoidance of trauma, treatment of infection and debridement of necrotic tissue. Gangrene is usually found on the toes. It develops when the blood supply is so low that spontaneous necrosis occurs in the most poorly perfused tissues.

Treatment and prognosis of peripheral vascular disease can be influenced by lesion and patient characteristics, such as the site of the lesion, type of lesion (stenosis or occlusion, lesion length), arterial runoff, and clinical manifestation (Dormandy J A, Rutherford R B. Management of peripheral arterial disease (PAD): TASC Working Group. J Vasc Surg 2000; 31 (1 pt 2):S103-S106). Estimates of the 5-year patency rate of balloon dilation for femoropopliteal arterial disease range from as low as 12% in patients with an occlusion and critical ischemia to 68% in patients with a stenosis and claudication (Hunink M G M, Wong J B, Donaldson M C, Meyerovitz M F, Harrington D P. Patency results of percutaneous and surgical revascularization for femoropopliteal arterial disease. Med Decis Making 1994; 14:71-81). Bypass surgery for femoropopliteal arterial disease has been associated not only with higher long-term patency rates but also with a higher procedural morbidity, mortality, and a longer hospital stay (Hunink M G M, Wong J B, Donaldson M C, Meyerovitz M F, de Vries J A, Harrington D P. Revascularization for femoropopliteal disease. A decision and cost-effectiveness analysis. JAMA 1995; 274:165-171).

Methods of treating peripheral vascular disease (PVD), including critical limb ischemia (CLI), preferably comprise the endovascular implantation of one or more coated medical devices provided herein. Atherosclerosis underlies many cases of peripheral vascular disease, as narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

Although exemplary embodiments of the invention have been described with respect to the treatment of complications such as restenosis following an angioplasty procedure, the local delivery of therapeutic agents may be used to treat a wide variety of conditions using any number of medical devices. For example, other medical devices that often fail due to tissue ingrowth or accumulation of proteinaceous material in, on, or around the device may also benefit from the present invention. Such devices may include, but are not limited to, intraocular lenses, shunts for hydrocephalus, dialysis grafts, colostomy bag attachment devices, ear drainage tubes, leads for pace makers, and implantable defibrillators.

A consensus document has been assembled by clinical, academic, and industrial investigators engaged in preclinical interventional device evaluation to set forth standards for evaluating drug-eluting stents such as those contemplated by the present invention. See "Drug-Eluting Stents in Preclinical Studies—Recommended Evaluation From a Consensus Group" by Schwartz and Edelman (available at "http://www.circulationaha.org") (incorporated herein by reference).

EXAMPLES

Example 1

Analysis of Liquid Spray Droplet Size

The droplet size of an isopropyl alcohol solution (200 proof) was measured at the center of a spray pattern at different distances, air pressure and liquid pressure settings using two different spray guns: an EFD 780S-SS spray valve system (EFD, Inc., East Providence, R.I.) (herein "EFD") and the Badger Airbrush (Model No. 200) ("BDGR"). The droplet diameter was measured using a Phase Doppler Particle Analyzer (PDPA) (SprayAnalysis and Research Services, Wheaton, Ill.). The Badger Airbrush nozzle was positioned within the center axis of the spray plume at a distance of 5 in. (127 mm) from the PDPA measurement location, while measurements from the EFD spray valve were performed at 7.5 in. (190.5 mm) and 9.5 in. (241.3 mm). The spray plumes tested in Example 1 consisted of 100% isopropyl alcohol, without any therapeutic agent or polymer material.

The PDPA measured particle droplet size with a 300 m-Watt Argon-Ion laser light source operated at an adequate power setting to offset any dense spray effects. The transmitter and receiver were mounted at a 37.5 degree forward scatter collection angle. The lens was a 250-mm focal length for the transmitter and a 300-mm for the receiver, resulting in a droplet measurement range of 0.5 micrometer to about 126.8 micrometers. The optical setup was used to ensure full range of droplet size measurement while maintaining good measurement resolution.

Table 1 shows the measurements of droplet diameter measurement parameters for three different measurements: EFD (9.5) and EFD (7.5) for the measurement of the EFD spray valve plume at a distance of 9.5 and 7.5 inches, respectively, and BDGR (5.0) for measurement of the Badger spray gun plume at a distance of 5.0 inches. Each measurement was performed for 20 seconds. The EFD spray plume was produced at a liquid pressure (i.e., tank pressure) of 2 psi and an air pressure (i.e., nozzle atomization pressure) of 13 psi and a temperature of 78 degrees F. The EFD (9.5) plume was measured at a relative humidity of 36.5%, while the EFD (7.5) plume was measured at a relative humidity of 26.0%. The BDGR (5.0) plume was obtained at an air pressure of 50 psi.

The particle distribution in each spray plume was characterized by the following parameters: $D_{0.1}$ refers to the particle diameter where 10% of the total volume of liquid sprayed is made up of drops with diameters smaller or equal to this value; $D_{0.5}$ refers to the particle diameter where 50% of the total volume of liquid sprayed is made up of drops with diameters smaller or equal to this value (i.e., the Volume Median Diameter); $D_{0.9}$ refers to the particle diameter where 90% of the total volume of liquid sprayed is made up of drops with diameters smaller or equal to this value; and $D_{32}$ refers to the particle diameter of a drop having the same volume to surface area ratio as the total volume of all the drops to the total surface area of all the drops (i.e., the Sauter Mean Diameter).

TABLE 1

|  | $D_{0.1}$ (µm) | $D_{0.5}$ (µm) | $D_{32}$ (µm) | $D_{0.9}$ (µm) |
| --- | --- | --- | --- | --- |
| EFD (9.5) | 5.2 | 12.9 | 10.8 | 23.0 |
| EFD (7.5) | 6.1 | 13.2 | 11.9 | 21.7 |
| BDGR (5.0) | 2.1 | 5.4 | 5.1 | 9.9 |

In addition, decreases in the air pressure of the EFD spray valve resulted in corresponding increases in the droplet sizes in the spray plume. For example, decreases in the air pressure from 13 psi to 10 psi, and from 10 psi to 5 psi, showed dramatic increases in droplet size at a given distance with decreases in the air pressure. Table 2 shows particle diameter measurements from the EFD spray valve all taken at a distance of 9.5 inches from the nozzle, in the center of the spray plume, at three different air pressures: 13, 10 and 5 psi. Notably, the diameter of the spray liquid particles decreased with increasing the air pressure.

TABLE 2

|  | $D_{0.1}$ (µm) | $D_{0.5}$ (µm) | $D_{32}$ (µm) | $D_{0.9}$ (µm) |
| --- | --- | --- | --- | --- |
| EFD (13 psi) | 5.2 | 12.9 | 10.8 | 23.0 |
| EFD (10 psi) | 8.1 | 18.2 | 16.1 | 30.6 |
| EFD (5 psi) | 14.3 | 35.7 | 29.0 | 63.9 |

Example 2

Paclitaxel Coating of Vascular Support Frames

A total of 40 10×30 mm Zilver® radially-expandable vascular support frames (Cook, Inc., Bloomington, Ind.) with radially compressed diameters of 7-French were coated in the expanded state by spray coating the abluminal surface (170 mm$^2$) with a solution consisting of 4 mg of paclitaxel ("PTX") per 1 mL of ethanol ("etoh") to form a paclitaxel-ethanol solution (about 4.7 mM). The stents were divided into two groups, A and B, and spray coated using the EFD spray gun at different nozzle atomization pressures and tank pressures, as detailed in Table 3. Preferably, the samples are coated in the lowest attainable humidity and the difference in humidity between samples was no more than about 5%. The humidity is desirably less than 40%, preferably less than 35%, more preferably less than 25% and most preferably less than about 15% relative humidity where the spray coating is performed. The stents in Group A were coated at a lower atomization pressure than the stents in Group B. The spray configuration is described with respect to FIG. 4 above. About 300-400 mg of paclitaxel was applied to the abluminal surface of each stent. Table 3 indicates the average amount of paclitaxel applied to the stents in each group. Following coating, the stents were inspected, photographed, crimped and loaded into delivery systems and EtO sterilized.

TABLE 3

Paclitaxel Coating of Stents

| Parameter | Group A (low pressure) | Group B (high pressure) |
|---|---|---|
| Solution tank pressure (psi) | 2.00 | 1.50 |
| Nozzle atomization pressure (psi) | 13 | 25 |
| Coating solution concentration | 4 mg PTX/ml etoh | 4 mg PTX/ml etoh |
| Coating hood relative humidity at start of run (%) | 28.0 | 30.2 |
| Coating hood temperature at start of run (F.) | 74.5 | 74.5 |
| Dose applied (μg) | 330 | 378 |

Example 3

Elution of Paclitaxel from Coated Stents

The rate of paclitaxel elution in each of the paclitaxel-coated stents described in Example 2 was analyzed in a modified porcine serum. The coated stents were contacted with a modified porcine serum elution medium at a constant flow rate of 16 mL/min for a desired period of time (e.g., 6-24 hours) selected to gradually dissolve the paclitaxel at a rate similar to dissolution in blood. The percentage of the paclitaxel dissolved can be measured as a function of time by monitoring the optical density of the modified porcine serum elution medium at 227 n=after contact with the coated stent. The modified porcine serum elution medium can be prepared by adding 0.104 mL of a 6.0 g/L Heparin solution to porcine serum at 37° C. and adjusting the pH to 5.6+/−0.3 using a 20% v/v aqueous solution of acetic acid.

Paclitaxel coatings applied at higher atomization pressures, on average, eluted more rapidly in the modified porcine serum elution medium than comparable coatings applied at lower atomization pressures. Table 4A and Table 4B provide a summary of the elution rate of the paclitaxel coatings of Group A and Group B, respectively. Each table indicates the number of coated stents tested, and the minimum, maximum and average percentage of paclitaxel released from the coated stent at a given time period of contact with the elution medium. For example, in Table 4A, of the 129 coated stents contacted with the elution medium for 20 minutes, between 37 and 83% of the paclitaxel was released from the coating, with an average of about 64% paclitaxel elution Comparatively, in Table 4B, an average of about 70% of the paclitaxel was released from the coating in the same time period from stents coated with a higher atomization pressure.

TABLE 4A

Low Atomization (13 psi)

| | 20 min | 45 min | 360 min |
|---|---|---|---|
| n= | 129 | 129 | 129 |
| min | 37 | 53 | 66 |
| max | 83 | 96 | 109 |
| Avg | 63.18 | 76.09 | 92.5 |
| Std Dev. | 10.53 | 9.67 | 7.04 |

TABLE 4B

High Atomization (25 psi)

| | 20 min | 45 min | 360 min |
|---|---|---|---|
| n= | 80 | 80 | 80 |
| min | 50 | 50 | 45 |
| max | 89 | 99 | 108 |
| Avg | 69.76 | 81.89 | 89.14 |
| Std Dev. | 8.55 | 7.74 | 7.92 |

As shown by the data in Table 4A and Table 4B, increasing the atomization pressure of the LED spray gun resulted in paclitaxel coatings with higher average elution rates in the modified porcine serum elution medium. Typically, the paclitaxel coatings applied at about 25 psi atomization pressure, on average, eluted about 3-6% faster than the paclitaxel coatings applied at about 13 psi atomization pressure.

Example 4

Paclitaxel Coating of Inflatable Balloon Catheters

The balloon portion of a tapered catheter balloon (Cook, Inc., Bloomington, Ind.) was coated with paclitaxel in the manner described with respect to Example 2 above, except as indicated in this example. The catheter balloon was coated in the expanded state with an abluminal surface area of about 218 mm$^2$ by spray coating the surface with a solution consisting of 12 mg of paclitaxel ("PTX") per 1 mL of ethanol ("etoh") to form a paclitaxel-ethanol solution (about 14 mM). A dose of about 3 micrograms/mm$^2$ of balloon surface area was applied. Alternatively, the increasing the solution tank pressure up to about 5 psi may increase the amount of the paclitaxel applied to the surface in a given period of coating time (i.e., increasing the throughput of the spray gun). Optionally, the concentration of paclitaxel in the ethanol spray solution may be varied between about 2 mg/mL and about 12 mg/mL (i.e., about 2.34 to 14.04 mM) to select a desired concentration of the paclitaxel in the coating, for example to increase the concentration of the paclitaxel in one spatially defined region of the coating. The solution was spray coated with the atomization spray gun used in Example 2 at the nozzle atomization pressures and tank pressures, as detailed in Table 5. About 650 mg of paclitaxel was applied to the abluminal surface of the balloon. Table 5 indicates the average amount of paclitaxel applied to the stents in each group. It is believed that spray coating paclitaxel using a higher atomization pressure at the proximal and distal tapered portions of the balloon may increase the dissolution rate of the paclitaxel in these regions. In addition, increasing the solution tank pressure while coating these regions compared to the central region between these portions of the balloon may increase the concentration of the paclitaxel. By increasing the dissolution rate and/or the concentration of the paclitaxel over the distal and proximal tapered ends, the coating may dissolve more rapidly from the balloon in regions that are not necessarily maintained in constant contact with the vessel wall during inflation of the balloon in the body vessel. By comparison, the central region of the balloon is likely to rapidly release the paclitaxel coating due to the hydrophobic attraction of the drug for the tissue of the vessel wall.

TABLE 5

Paclitaxel Coating of Stents

| Parameter | Group C (Catheter Balloons) |
| --- | --- |
| Solution tank pressure (psi) | 2.00 |
| Nozzle atomization pressure (psi) | 16 |
| Coating solution concentration | 12 mg PTX/ml etoh |
| Coating hood relative humidity at start of run (%) | 12.0 |
| Coating hood temperature at start of run (F.) | 80 |
| Dose applied (μg) | 655 |

The invention includes other embodiments within the scope of the claims, and variations of all embodiments. Although exemplary embodiments of the invention have been described with respect to the treatment of complications such as restenosis following an angioplasty procedure, the local delivery of therapeutic agents may be used to treat a wide variety of conditions using any number of medical devices.

We claim:

1. An implantable medical device having a coating on an abluminal surface extending from a proximal end to a distal end, the coating formed by the steps of:
    spraying droplets having a first average liquid droplet size and comprising a solution of a volatile solvent and a taxane therapeutic agent onto a first region of the abluminal surface;
    evaporating the volatile solvent to form a coating of the taxane therapeutic agent on the first region;
    spraying droplets having a second average liquid droplet size and comprising the solution of the volatile solvent and the taxane therapeutic agent onto a second region of the abluminal surface;
    wherein the second average liquid droplet size is greater than the first average liquid droplet size; and
    evaporating the volatile solvent to form a coating of the taxane therapeutic agent on the second region, wherein release of the taxane therapeutic agent from the first region in an aqueous medium is faster than release of the taxane therapeutic agent from the second region in the aqueous medium, and
    wherein the coating consists essentially of the taxane therapeutic agent and an antithrombotic agent on the first region and on the second region and does not include a polymer.

2. The coated implantable medical device of claim 1, where the coating consists essentially of a particulate coating on the abluminal surface comprising:
    a. the first region including the plurality of first particles comprising the taxane therapeutic agent and having a first average diameter, the first region extending from the distal end to the second region; and
    b. the second region including the plurality of second particles comprising the taxane therapeutic agent and having a second average diameter, the second region positioned proximal to the first region.

3. The coated medical device of claim 2, wherein the first average diameter and the second average diameter are both between about 1 to 100 micrometers.

4. The coated medical device of claim 2, wherein the second average diameter is at least 60% larger than the first average diameter.

5. The coated medical device of claim 2, wherein the first average diameter is between 1 and 20 micrometers and the second average diameter is between 30 and 50 micrometers.

6. The coated medical device of claim 2, wherein the taxane therapeutic agent in the first region elutes at least about 15% faster than the taxane therapeutic agent in the second region when contacted with a porcine serum elution medium prepared by adding 0.104 mL of a 6.0 g/L heparin solution to porcine serum at 37° C. and adjusting the pH to 5.6+/−0.3 using a 20% v/v aqueous solution of acetic acid.

7. The coated medical device of claim 2, where the coating on the abluminal surface further comprises: a third region including a plurality of third particles comprising the taxane therapeutic agent and having a third average diameter that is less than the second average diameter, the third region positioned between the distal end and the second region.

8. The coated medical device of claim 2, where the medical device is a catheter balloon, a radially expandable vascular support frame or the vascular support frame disposed around a balloon portion of the catheter balloon;
    a. where the particulate coating on the abluminal surface of the medical device further comprises a third region including a plurality of third particles comprising the taxane therapeutic agent and having a third average diameter that is less than the second average diameter, the third region positioned between the distal end and the second region; and where
        i. the first region and the second region are contained within a continuous layer of the particulate coating;
        ii. the particulate coating is a single-layer coating;
        iii. the taxane therapeutic agent is paclitaxel;
        iv. the first region elutes at a faster rate than the second region when contacted with an ethanol elution medium;
        v. the first region comprises a first concentration of the paclitaxel that is greater than the concentration of the paclitaxel in the second region;
        vi. the first region elutes at least about 15% faster than the second region when contacted with a porcine serum elution medium prepared by adding 0.104 mL of a 6.0 g/L heparin solution to porcine serum at 37° C. and adjusting the pH to 5.6+/−0.3 using a 20% v/v aqueous solution of acetic acid;
        vii. the first region comprises about 3-10 micrograms paclitaxel per $mm^2$ of the coated abluminal surface area of the first region, and the second region comprises about 0.1-2.0 micrograms of paclitaxel per $mm^2$ of the coated abluminal surface area of the second region;
        viii. the first region and the second region contain particles with a first average diameter of the first particles and the second average diameter of the second particles both being between about 1 to 100 micrometers, with the first average diameter being between about 1 and 20 micrometers and the second average diameter being about 30 micrometers to about 50 micrometers; and where the second average diameter is at least 60% larger than the first average diameter; and
        ix. the coating is free of a polymer; and where b. the first region is formed by spraying the solution at a first atomization pressure and the second region is formed by spraying the solution at a second atomization pressure.

9. The coated medical device of claim 1, wherein the first region and the second region are contained within a continuous layer of the coating.

10. The coated medical device of claim 1, wherein the coating is a single-layer coating.

11. The coated medical device of claim 1, wherein the taxane therapeutic agent is paclitaxel.

12. The coated medical device of claim 1, wherein the first region comprises a first concentration of the taxane therapeutic agent and the second region comprises a second concentration of the taxane-therapeutic agent, wherein the first concentration is greater than the second concentration.

13. The coated medical device of claim 12, wherein the taxane therapeutic agent is paclitaxel and wherein the first region comprises about 3-10 micrograms of paclitaxel per mm$^2$ of the coated abluminal surface area of the first region, and the second region comprises about 0.1-2.0 micrograms of paclitaxel per mm$^2$ of the coated abluminal surface area of the second region.

14. The coated medical device of claim 1, wherein the implantable medical device is a balloon catheter having a balloon comprising the abluminal surface.

15. The coated medical device of claim 1, wherein the first region is coated by spraying the solution at a first atomization pressure and the second region is coated by spraying the solution at a second atomization pressure.

16. The coated medical device of claim 1, wherein the first region elutes at a faster rate than the second region when contacted with a porcine serum elution medium prepared by adding 0.104 mL of a 6.0 g/L heparin solution to porcine serum at 37° C. and adjusting the pH to 5.6+/−0.3 using a 20% v/v aqueous solution of acetic acid.

17. The coated medical device of claim 1, wherein the coating of the taxane therapeutic agent on the first and second regions contains less than 0.1 microgram per mm$^2$ of a non-polymer carrier modifying a rate of release of the therapeutic agent.

18. The coated medical device of claim 1, wherein the coating of the taxane therapeutic agent on the first and second regions consists essentially of the taxane therapeutic agent.

19. The coated medical device of claim 1, wherein the droplets having a first average liquid droplet size and the droplets having a first average liquid droplet size consist essentially of a solution of the volatile solvent and the taxane therapeutic agent.

20. An implantable medical device having a coating on an abluminal surface extending from a proximal end to a distal end, the coating formed by the steps of:
spraying droplets having a first average liquid droplet size and comprising a solution of a volatile solvent and a taxane therapeutic agent onto a first region of the abluminal surface;
evaporating the volatile solvent to form a coating of the taxane therapeutic agent on the first region;
spraying droplets having a second average liquid droplet size and comprising the solution of the volatile solvent and the taxane therapeutic agent onto a second region of the abluminal surface;
wherein the second average liquid droplet size is greater than the first average liquid droplet size; and
evaporating the volatile solvent to form a coating of the taxane therapeutic agent on the second region, wherein release of the taxane therapeutic agent from the first region in an aqueous medium is faster than release of the taxane therapeutic agent from the second region in the aqueous medium,
wherein the coating of the taxane therapeutic agent on the first region and on the second region does not include a polymer; and
where the coating consists essentially of a particulate coating on the abluminal surface comprising:
a. the first region including the plurality of first particles comprising the taxane therapeutic agent and having a first average diameter, the first region extending from the distal end to the second region; and
b. the second region including the plurality of second particles comprising the taxane therapeutic agent and having a second average diameter, the second region positioned proximal to the first region; and
wherein the taxane therapeutic agent is paclitaxel and wherein the first region comprises about 3-10 micrograms of paclitaxel per mm$^2$ of the coated abluminal surface area of the first region, and the second region comprises about 0.1-2.0 micrograms of paclitaxel per mm$^2$ of the coated abluminal surface area of the second region.

21. An implantable medical device having a coating on an abluminal surface extending from a proximal end to a distal end, the coating formed by the steps of:
spraying droplets having a first average liquid droplet size and comprising a solution of a volatile solvent and a taxane therapeutic agent onto a first region of the abluminal surface;
evaporating the volatile solvent to form a coating of the taxane therapeutic agent on the first region;
spraying droplets having a second average liquid droplet size and comprising the solution of the volatile solvent and the taxane therapeutic agent onto a second region of the abluminal surface;
wherein the second average liquid droplet size is greater than the first average liquid droplet size; and
evaporating the volatile solvent to form a coating of the taxane therapeutic agent on the second region, wherein release of the taxane therapeutic agent from the first region in an aqueous medium is faster than release of the taxane therapeutic agent from the second region in the aqueous medium,
wherein the coating of the taxane therapeutic agent on the first region and on the second region does not include a polymer; and
where the coating consists essentially of a particulate coating on the abluminal surface comprising:
a. the first region including the plurality of first particles comprising the taxane therapeutic agent and having a first average diameter, the first region extending from the distal end to the second region; and
b. the second region including the plurality of second particles comprising the taxane therapeutic agent and having a second average diameter, the second region positioned proximal to the first region; and
wherein the first average diameter is between 1 and 20 micrometers and the second average diameter is between 30 and 50 micrometers.

* * * * *